(12) United States Patent
Fan et al.

(10) Patent No.: US 10,400,228 B2
(45) Date of Patent: Sep. 3, 2019

(54) TRUNCATED PULLULANASES, METHODS OF PRODUCTION, AND METHODS OF USE THEREOF

(71) Applicant: Nanjing Bestzyme Bio-Engineering Co., Ltd., Nanjing (CN)

(72) Inventors: Yan Fan, Nanjing (CN); Yamin Lu, Nanjing (CN); Xiuzhen Du, Nanjing (CN); Huadong Du, Nanjing (CN); Feng Li, Nanjing (CN)

(73) Assignee: NANJING BESTZYME BIO-ENGINEERING CO., LTD., Nanjing (CN)

(*) Notice: Subject to any disclaimer, the term of this patent is extended or adjusted under 35 U.S.C. 154(b) by 10 days.

(21) Appl. No.: 15/113,077

(22) PCT Filed: Nov. 10, 2015

(86) PCT No.: PCT/US2015/059914
§ 371 (c)(1),
(2) Date: Jul. 21, 2016

(87) PCT Pub. No.: WO2016/126294
PCT Pub. Date: Aug. 11, 2016

(65) Prior Publication Data
US 2016/0369254 A1    Dec. 22, 2016

(30) Foreign Application Priority Data
Feb. 4, 2015    (CN) .......................... 2015 1 0059495

(51) Int. Cl.
| | |
|---|---|
| *C12P 21/02* | (2006.01) |
| *C07K 14/32* | (2006.01) |
| *C12N 9/44* | (2006.01) |
| *C12P 19/04* | (2006.01) |
| *C12P 19/14* | (2006.01) |
| *C12P 19/02* | (2006.01) |
| *C12P 19/16* | (2006.01) |

(52) U.S. Cl.
CPC ............ *C12N 9/2457* (2013.01); *C12P 19/02* (2013.01); *C12P 19/04* (2013.01); *C12P 19/14* (2013.01); *C12P 19/16* (2013.01); *C12Y 302/01041* (2013.01)

(58) Field of Classification Search
CPC .......... C12N 9/44; D06M 16/00; C12P 21/02; C07K 14/4732
See application file for complete search history.

(56) References Cited

U.S. PATENT DOCUMENTS

| | | | |
|---|---|---|---|
| 6,074,854 A | 6/2000 | Deweer et al. | |
| 7,449,320 B2 * | 11/2008 | Miller ................. | C12N 9/2451 435/210 |
| 7,906,306 B2 | 3/2011 | Svendsen | |
| 7,968,691 B2 * | 6/2011 | England .......... | C12Y 302/0104 424/94.1 |
| 2003/0013180 A1 | 1/2003 | Miller et al. | |
| 2004/0048247 A1 | 3/2004 | Svendsen et al. | |
| 2011/0281326 A1 | 11/2011 | England et al. | |

FOREIGN PATENT DOCUMENTS

| | | |
|---|---|---|
| CN | 103571812 A | 2/2014 |
| JP | 2002505108 A | 2/2002 |
| JP | 2010501181 A | 1/2010 |
| WO | 9945124 A2 | 9/1999 |
| WO | 200151620 A2 | 7/2001 |
| WO | 20080024372 A2 | 2/2008 |

OTHER PUBLICATIONS

Wallenfels et al., "Pullulanase from Aero bacter Aerogenes; Production in a Cell-Bound State. Purification and Properties of the Enzyme", Biochemical and Biophysical Research Communication, vol. 22, No. 3, pp. 254-261 (1996).
Int'l Search Report dated Feb. 5, 2016 in Int'l Application No. PCT/US2015/059914.
Bakshi et al, "Thermostable Pullulanase from a Masophilic Bacillus Cereus Isolate and its Mutant UV7.4," Biotechnol. Lett., vol. 14, No. 8, pp. 689-694 (1992).
Chang et al,"High Frequency Transformation of Bacillus Subtilis Protoplasts by Plasmid DNA," Mol. Gen. Genet., vol. 168, pp. 111-115 (1979).
D'Enfert et al,"Cloning and Expression in *Escherichia Coli* of the Klebsiella pneumoniae Genes for Production, Surface Localization and Secretion of the Lipoprotein Pullulanase," EMBO J., vol. 6, No. 11, pp. 3531-3538 (1987).
Horinouchi et al, "Nucleotide Sequence and Functional Map of pE194, A Plasmid That Specifies Inducible Resistance to Macrolide, Lincosamide, and Streptogramin Type B Antibodies," J. Bacteriol, vol. 150, No. 2, pp. 804-814 (1982).
Koch et al,"Purification and Properties of a Thermostable Pullulanase from a Newly Isolated Thermophilic Anaerobic Bacterium, Fervidobacterium pennavorans Ven5," Appl. Environ. Microbiol., vol. 63, No. 3, pp. 1088-1094 (1997).
Kusano et al, "Purification and Properties of Bacillus acidopullulyticus Pullulanase," Agric.Biol. Chem., vol. 52, No. 9, pp. 2293-2298 (1988).

(Continued)

*Primary Examiner* — Maryam Monshipouri
(74) *Attorney, Agent, or Firm* — Panitch Schwarze Belisario & Nadel LLP

(57) ABSTRACT

Truncated pullulanases having an N-terminal deletion in a parental pullulanase are provided. These truncated pullulanases have altered properties as compared to the parental pullulanase, including an increased saccharification rate and higher catalytic activity at acidic pH values below 4.5 and higher temperatures of up to 64° C. These truncated pullulanase also have improved thermal stability as compared to the parental enzyme. Also provided are compositions containing the truncated pullulanases and a glucoamylase, and processes for applying the truncated pullulanases and compositions in the starch industry. Polynucleotides that encode the truncated pullulanases, and recombinant host cells for producing the truncated pullulanases are also described.

12 Claims, 2 Drawing Sheets
Specification includes a Sequence Listing.

(56) References Cited

OTHER PUBLICATIONS

Lappalainen et al.,"Purification and Characterization of Bacillus acidopullulyticus Pullulanase for Enzymatic Starch Modification," Starch, vol. 43, No. 12, pp. 477-482 (1991).
Nelson, "A Photometric Adaptation of the Somogyi Method for the Determination of Glucose," J. Biol. Chem., vol. 153, pp. 375-380 (1944).
Norman, "A Novel Debranching Enzyme for Application in the Glucose Syrup Industry," Starch, vol. 34, No. 10, pp. 340-346 (1982).
Odibo et al, "Purification and Characterization of a Thermostable Pullulanase from Thermoactinomyces thalpophilus," J.Industr. Microbiol., vol. 3, pp. 343-350 (1988).
Turkenburg et al, "Structure of a Pullulanase from Bacillus Acidopullulyticus," Proteins vol. 76, pp. 516-519 (2009).
Widner et al, "Development of Marker-Free Strains of Bacillus subtilis Capable of Secreting High Levels of Industrial Enzymes," J. Industr. Microbiol. Biotech., vol. 25, pp. 204-212 (2000).
Young et al, "Physiological and Genetic Factors Affecting Transformation of Bacillus subtilis," J. Bacteriol., vol. 81, pp. 823-829 (1961).
Nakamura et al, "Purification and Some Properties of Alkaline Pullulanase from a Strain of Bacillus No. 202-1, an Alkalophilic Microorganism," Biochim.Biophys.Acta, vol. 397, pp. 188-193 (1975). Abstract Only.
Duan et al., "Enhancing the Secretion Efficiency and Thermostability of a Bacillus deramificans Pullulanase Mutant (D437H/D503Y) byt N-Terminal Domain Truncation," Appl. Environ. Microbiol., vol. 81, No. 6, pp. 1926-1931 (Jan. 2, 2015).
Extended European Search Report dated Oct. 10, 2018 in EP Application No, 15881388.1.
Office Action dated Jul. 31, 2018 in JP Application No. 2017541856.
Svendsen et al, "Bacillus acidopullulytious pullulanse promozyme," Database Accession No. AAE05689- & Database EPO Proteins [Online] (Sep. 24, 2001).
Svendsen et al., "Sequence 4 from Patent WO 0151620," XP002784920, Database Accession No. AX203846 (May 31, 2006).

* cited by examiner

TRUNCATED PULLULANASES, METHODS OF PRODUCTION, AND METHODS OF USE THEREOF

CROSS-REFERENCE TO RELATED APPLICATION

This application is a Section 371 of International Application No. PCT/US2015/059914, filed Nov. 10, 2015, and the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688096_64U1_Sequence_Listing" and a creation date of Nov. 10, 2015, and having a size of 70 kB. The sequence listing submitted via EFS-Web is part of the specification and is herein incorporated by reference in its entirety.

BACKGROUND OF THE INVENTION

Starch extracted from corn, cassava, rice, potatoes and wheat serves as a major source of raw materials for the large-scale production of sugars and derivatives in the starch industry. General starch is usually made up of two types of macromolecules, amylose and amylopectin, and the relative amounts of each mainly depend on the source species. Amylose is a linear polysaccharide comprised of glucose residues linked only by α-1,4-glucosidic bonds, whereas in amylopectin, besides the α-1,4-glucosidic bonds, glucose residues are also joined by α-1,6-glucosidic linkages to form branch points. In order to degrade the starch and obtain simple sugars, the starch is initially depolymerized by heat stable α-amylase, which partially hydrolyzes the α-1,4-glucosidic bonds, followed by a saccharification step, in which the smaller branched and linear units are further converted into glucose or maltose by addition of a glucoamylase or beta-amylase (Norman, 1982).

It has been proposed that the addition of a debranching enzyme that is capable of hydrolyzing α-1,6-glucosidic bonds during the saccharification step of starch can yield higher purity glucose and maltose syrups. Meanwhile, the debranching enzyme can reduce saccharification time and increase the applied substrate concentrations (Bakshi et al., 1992). Nowadays, this application has been widely used in industry, such as for starch conversion, beer brewing, and amylose production.

Pullulanase (pullulan 6-glucanohydrolases, EC 3.2.1.41) is classified as a debranching enzyme that specifically hydrolyzes α-1,6-glucosidic bonds in starch, pullulan, and related branched polysaccharides. Given the growing demand for the improvement of such enzymatic technology and reduction of production costs during the saccharification of starch, seeking improved pullulanases that are more efficient in starch conversion has become an important area for both industry and academia.

Many microbial pullulanases have been found and characterized from plants and bacteria, including *Klebsiella pneumonia* (d'Enfert, Ryter et al. 1987), *Fervidobacterium pennavorans* (Koch. Canganella et al. 1997), *Thermoactinomyces thalpophilus* (Odibo et al. 1988), and *Bacillus* species (Nakamura, Watanabe et al. 1975). Modified pullulanase enzymes derived from bacterial pullulanases have also been reported (e.g., U.S. Pat. No. 7,906,306, U.S. Pat. No. 7,449,320, and U.S. Pat. No. 7,968,691). For example, U.S. Pat. No. 7,449,320 reports a mixture of truncated forms of pullulanases derived from a native bacterial pullulanase (SEQ ID NO: 25) having N-terminal deletions of 98 and 102 amino acid residues obtained from cleavage of the mature pullulanase by extracellular proteases of the recombinant host cell. This mixture was reported to be most stable at a pH of 4.5. However, the truncated forms were not isolated, nor was the activity of the mixture compared to the activity of the untruncated mature form.

U.S. Pat. No. 7,968,691 discloses a truncated pullulanase derived from a native bacterial pullulanase having an N-terminal deletion of 104 amino acids. Pullulanase activity was tested by transforming a plasmid encoding the truncated pullulanase into *B. subtilis*, and screening for halo formation in a pullulan overly assay (0.1% in 100 mM NaAc pH 5.0, 1%).

The most commercially valuable pullulanases are pullulanases from *Bacillus* species, particularly *Bacillus acidopullulyticus* (Lappalainen et al., 1991; Kusano et al., 1988) and *Bacillus deramificans* (Deweer et al. U.S. Pat. No. 6,074,854, 2000). These pullulanases have a molecular mass of about 100 kD, which is similar to pullulanases obtained from other sources, and have the ability to hydrolyze α-1,6-glucosidic bonds at an acidic pH at 60° C. Although suitable for the production of high-purity glucose and maltose in the starch industry, the pullulanases from *Bacillus acidopullulyticus* and *Bacillus deramificans* exhibit a slow saccharification rate, and decreased enzyme activity at increased temperatures and low pH, particularly at temperatures over 60° C. and pH values lower than 4.5, conditions that are often used for controlling industrial processes.

Accordingly, there exists a need in the art for improved pullulanase enzymes that have an increased saccharification rate, and improved enzymatic activity at temperatures over 60° C. and acidic pH values below 4.5.

BRIEF SUMMARY OF THE INVENTION

The invention satisfies this need by providing truncated pullulanase enzymes that have an improved ability to catalyze saccharification of α-1,6-glucosidic linkages as compared to a corresponding parental pullulanase enzyme. In particular, the truncated pullulanase enzymes of the present invention exhibit improved enzymatic activity at temperatures over 60° C. and acidic pH values below 4.5, as compared to the enzymatic activity of the corresponding parental pullulanase enzyme.

In one general aspect, the invention relates to an isolated or purified truncated pullulanase comprising a deletion of 94 to 115 amino acid residues from the amino terminus of a parental pullulanase, wherein the parental pullulanase comprises the amino acid sequence of SEQ ID NO: 2 or SEQ ID NO: 4.

According to particular embodiments of the invention, a truncated pullulanase comprises a deletion of 94 amino acids, 102 amino acids, or 104 amino acids from the amino terminus of the parental pullulanase. In other particular embodiments, a truncated pullulanase consists of the amino acid sequence of SEQ ID NOs: 6, 8, or 9.

In another general aspect, the invention relates to a method of hydrolyzing an α-1,6-glucosidic linkage in a carbohydrate, comprising contacting the carbohydrate with an isolated or purified truncated pullulanase according to the invention under a condition suitable for hydrolyzing the α-1,6-glucosidic linkage.

In another general aspect, the invention relates to a method of catalyzing a saccharification of a carbohydrate having one or more α-1,6-glucosidic linkages comprising contacting the carbohydrate with an isolated or truncated pullulanase comprising a deletion of 94 to 115 amino acids from the amino terminus of the parental pullulanase under a condition suitable for the saccharification, wherein the condition comprises at least one of a pH of 4.5 or less and a temperature of 60° C. or higher, and wherein the parental pullulanase comprises the amino acid sequence of SEQ ID NO: 2 or SEQ ID NO: 4.

In another general aspect, the invention relates to a method of catalyzing a saccharification of a carbohydrate having one or more α-1,6-glucosidic linkages comprising contacting the carbohydrate with a glucoamylase and an isolated or truncated pullulanase comprising a deletion of 94 to 115 amino acids from the amino terminus of the parental pullulanase under a condition suitable for the saccharification, wherein the condition comprises at least one of a pH of 4.5 or less and a temperature of 60° C. or higher, and wherein the parental pullulanase comprises the amino acid sequence of SEQ ID NO: 2 or SEQ ID NO: 4.

In yet another general aspect, the invention relates to a system for catalyzing saccharification of a carbohydrate having one or more α-1,6-glucosidic linkages, comprising the carbohydrate, a glucoamylase, and an isolated or purified truncated pullulanase comprising a deletion of 94 to 115 amino acids from the amino terminus of a parental pullulanase under a condition suitable for the saccharification, wherein the condition comprises at least one of a pH of 4.5 or less and a temperature of 60° C. or higher, wherein the parental pullulanase comprises the amino acid sequence of SEQ ID NO: 2 or SEQ ID NO: 4.

In particular embodiments of the invention, the truncated pullulanase consists of an amino acid selected from the group consisting of SEQ ID NO: 6, SEQ ID NO: 8, and SEQ ID NO: 9.

In yet another general aspect, the invention relates to a composition comprising a glucoamylase and an isolated or purified truncated pullulanase comprising a deletion of 94 to 115 amino acids from the amino terminus of a parental pullulanase, wherein the parental pullulanase comprises the amino acid sequence of SEQ ID NO: 2 or SEQ ID NO: 4.

And in yet another general aspect, the invention relates to a method of producing a truncated pullulanase according to the invention comprising:

(a) growing a recombinant host cell comprising a synthetic polynucleotide encoding the truncated pullulanase under conditions suitable for expression of the truncated pullulanase; and (b) obtaining the truncated pullulanase from the recombinant host cell or its supernatant.

Embodiments of the invention also relate to polynucleotides encoding a truncated pullulanase according to the invention, expression vectors comprising a synthetic polynucleotide encoding a truncated pullulanase according to the invention, and recombinant host cells comprising the expression vectors.

DETAILED DESCRIPTION OF THE INVENTION

Figure 1:
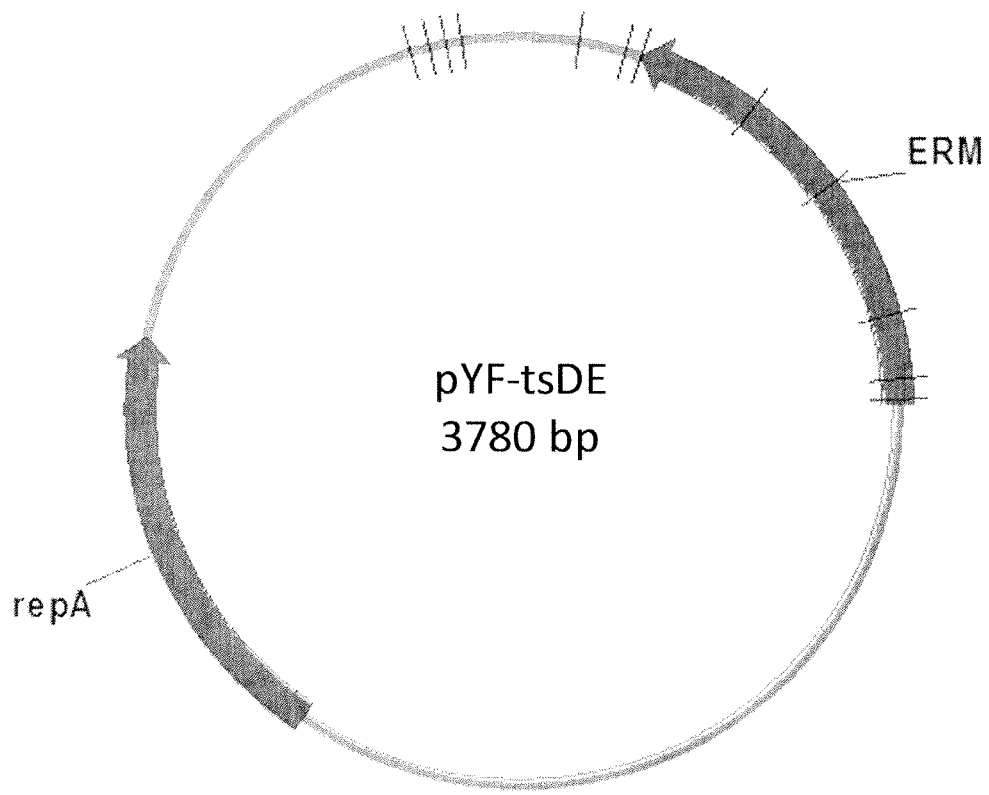
FIG. 1 is a schematic representation of an pYF-tsDE vector comprising a temperature-sensitive origin of replication active at 30° C. and an erythromycin determinant gene (ErmC) resistant to 300 µg/mL of erythromycin in *E. coli* and 5 µg/mL of erythromycin in *B. subtilis* that can be used to construct a recombinant host cell comprising a synthetic nucleic acid encoding a truncated pullulanase according to an embodiment of the invention.

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

As used herein, the terms "pullulanase" and "pullulanase enzyme" refer to an enzyme that is capable of hydrolyzing α-1,6-glucosidic linkages in polysaccharides. Pullulanase enzymes are also known as debranching enzymes, because they can hydrolyze α-1,6-glucosidic linkages in branched polysaccharides, such as starch, to yield straight chain polysaccharides, disaccharide, or monosaccharide components. For example, pullulanase enzymes can break down starch to yield straight chain amylose polymers, which are primarily polymers of α-1,4-linked glucose sugars.

As used herein, the terms "parental pullulanase" and "parental pullulanase enzyme" refer to a native pullulanase. Preferably, the native pullulanase is a bacterial pullulanase, including, but not limited to pullulanases from *Bacillus subtilis*, *Klebsiella pneumonia*, *Fervidobacterium pennavorans*, *Thermoactinomyces thalpophilus*, *Bacillus acidopullulyticus*, *Bacillus deramificans*, and *Bacillus cereus*.

According to preferred embodiments of the invention, a native pullulanase is a pullulanase from a *Bacillus* bacterial strain, preferably *Bacillus acidopullulyticus* or *Bacillus deramificans*. The full-length coding sequence of pullulanases obtainable from *Bacillus acidopullulyticus* and *Bacillus deramificans* are shown in SEQ ID NOs: 1 and 3, respectively. The corresponding amino acid sequences of these pullulanases are shown in SEQ ID NOs: 2 and 4, respectively.

As used herein, the term "truncated pullulanase" refers to a non-naturally occurring variant of a parental pullulanase having an N-terminal deletion of 94 to 115 amino acid residues from the amino terminus of the corresponding parental pullulanase, and which retains the ability to catalyze hydrolysis of α-1,6-glucosidic linkages. According to embodiments of the invention, the N-terminal deletion starts at the first amino acid residue, i.e., amino acid residue 1, of the amino acid sequence of the parental pullulanase.

The term "saccharification" as used herein is intended to generally refer to the process of breaking down a carbohydrate into smaller components including monosaccharides, disaccharides, and polysaccharides. When used with reference to a pullulanase enzyme or truncated pullulanase, the term "saccharification" specifically refers to the hydrolysis of α-1,6-glucosidic linkages in carbohydrates, and particularly α-1,6-glucosidic linkages in branched carbohydrates.

As used herein, the term "α-1,6-glucosidic linkage" refers to a bond formed between the C6 carbon of a first glucose sugar and an oxygen attached to the anomeric carbon (C1 carbon) of a second glucose sugar, with the second glucose sugar being an alpha anomer.

The invention relates to truncated pullulanases derived from a parental pullulanase. The parental pullulanase is a native pullulanase, and preferably a native bacterial pullulanase. According to embodiments of the invention, a truncated pullulanase comprises an N-terminal deletion of 94 to 115 amino acid residues in an amino acid sequence of the parental pullulanase enzyme, wherein the deletion starts at amino acid residue 1 of the parental pullulanase enzyme.

The invention also encompasses variants of truncated pullulanases. According to embodiments of the invention, a variant of a truncated pullulanase has an amino acid sequence that is at least 95% identical to an amino acid sequence of the truncated pullulanase enzyme, such as 95%, 96%, 97%, 98%, 99%, or 100% sequence identity. Truncated pullulanases can also be modified, e.g., by covalent linkage to a small molecule, at one or more amino acid residues.

According to embodiments of the invention, the deletion from the amino terminus of a parental pullulanase can be a deletion of 94 amino acid residues and up to 115 amino acid residues. The N-terminal deletion can be, for example, a deletion of amino acid residues 1 to 115; a deletion of amino acid residues 1 to 111; a deletion of amino acid residues 1 to 110; a deletion of amino acid residues 1 to 104; a deletion of amino acid residues 1 to 102; a deletion of amino acid residues 1 to 100; or a deletion of amino acid residues 1 to 94 starting from the amino terminus of the parental pullulanase.

According to preferred embodiments of the invention, a truncated pullulanase comprises a deletion of 94, 102, or 104 amino acids from the amino terminus of a parental pullulanase.

According to embodiments of the invention, the parental pullulanase enzyme is preferably a native bacterial pullulanase. Bacterial pullulanases, include, but are not limited to, pullulanases from *Bacillus subtilis*, *Klebsiella pneumonia*, *Fervidobacterium pennavorans*, *Thermoactinomyces thalpophilus*, *Bacillus acidopullulyticus*, *Bacillus deramificans*, and *Bacillus cereus*.

According to embodiments of the invention, the parental pullulanase is a pullulanase obtained from a *Bacillus* bacteria, preferably *Bacillus acidopullulyticus* or *Bacillus deramificans*, and more preferably *Bacillus deramificans*. In particular embodiments, the parental pullulanase is a *Bacillus acidopullulyticus* pullulanase having the amino acid sequence of SEQ ID NO: 2; or a *Bacillus deramificans* pullulanase having the amino acid sequence of SEQ ID NO: 4.

According to preferred embodiments of the invention, a truncated pullulanase is derived from a parental pullulanase that is a native *Bacillus deramificans* pullulanase having SEQ ID NO: 4. According to one preferred embodiment, amino acid residues 1 to 94 at the N-terminus of a parental pullulanase having SEQ ID NO: 4 are deleted to provide a truncated pullulanase comprising SEQ ID NO: 6. In another preferred embodiment, amino acid residues 1 to 104 at the N-terminus of a parental pullulanase having SEQ ID NO: 4 are deleted to provide a truncated pullulanase comprising SEQ ID NO: 8. Such truncated pullulanase enzymes according to the invention can be encoded by a polynucleotide sequence as shown in SEQ ID NO: 5 and SEQ ID NO: 7, respectively. In yet another preferred embodiment, amino acid residues 1 to 102 at the N-terminus of a parental pullulanase having SEQ ID NO: 4 are deleted to provide a truncated pullulanase comprising SEQ ID NO: 9.

In particular embodiments of the invention, a truncated pullulanase consists of the amino acid sequence of SEQ ID NO: 6, SEQ ID NO: 8, or SEQ ID NO: 9.

Truncated pullulanases according to the invention retain the ability to catalyze hydrolysis of α-1,6-glucosidic linkages. Additionally, these truncated pullulanases have improved properties as compared to the parental pullulanase, such as an increased saccharification rate, higher catalytic activity at acidic pH, and particularly below a pH value of 4.5, and higher catalytic activity at higher reaction temperatures.

According to embodiments of the invention, a truncated pullulanase has higher catalytic activity at acidic pH values below a pH of 4.5, and higher catalytic activity at temperatures above 60° C., particularly at temperatures in a range of 60° C. to 64° C., as compared to the catalytic activity of the corresponding parental pullulanase. These improved properties make the truncated pullulanases of the invention particularly desirable for formulations and processes used in the starch industry, at least because such processes are often conducted at pH values below 4.5 and/or temperatures above 60° C.

Thus, in another general aspect, the invention provides a method of hydrolyzing α-1,6-glucosidic linkages in a carbohydrate, comprising contacting the carbohydrate with an isolated or purified truncated pullulanase according to the invention under a condition suitable for the hydrolysis reaction. Any of the truncated pullulanases described herein can be used in a method of hydrolyzing α-1,6-glucosidic linkages according to the invention.

Any carbohydrate having one or more α-1,6-glucosidic linkages can be used in a method of hydrolyzing an α-1,6-glucosidic linkage according to the invention. Non-limiting examples of carbohydrates having one or more α-1,6-glucosidic linkages include starch, amylopectin, dextran, maltodextrin, pullulan, glycogen, etc.

The invention also provides a method of catalyzing saccharification of a carbohydrate having one or more α-1,6-glucosidic linkages. According to embodiments of the invention, the method comprises contacting the carbohydrate with an isolated or purified truncated pullulanase comprising a deletion of 94 to 115 amino acids from the amino terminus of a parental pullulanase under a condition suitable for the saccharification, wherein the condition comprises at least one of a pH of 4.5 or less and a temperature of 60° C. or higher, and wherein the parental pullulanase comprises the amino acid sequence of SEQ ID NO: 2 or SEQ ID NO: 4.

Many carbohydrates having α-1,6-glucosidic linkages further comprise α-1,4-glucosidic linkages, such as, for example, amylopectin. An "α-1,4-glucosidic linkage" refers to a bond formed between the C4 carbon of a first glucose sugar and the oxygen attached to the anomeric carbon of a second glucose sugar, with the second glucose sugar being an alpha anomer.

Thus, in yet another general aspect, the invention provides a method of catalyzing saccharification of a carbohydrate having one or more α-1,6-glucosidic linkages, the method comprising contacting the carbohydrate with a glucoamylase and an isolated or purified truncated pullulanase comprising a deletion of 94 to 115 amino acids from the amino terminus of a parental pullulanase under a condition suitable for the saccharification, wherein the condition comprises at least one of a pH of 4.5 or less and a temperature of 60° C.

or higher, and wherein the parental pullulanase comprises the amino acid sequence of SEQ ID NO: 2 or SEQ ID NO: 4.

Any of the truncated pullulanases described herein can be used in a method of saccharification according to the invention. In preferred embodiments, the truncated pullulanase is derived from a bacterial parental pullulanase, and more preferably is derived from a *Bacillus deramificans* parental pullulanase. In particularly preferred embodiments, the truncated pullulanase used in a method of the invention consists of the amino acid sequence of SEQ ID NO: 6, SEQ ID NO: 8, or SEQ ID NO: 9.

According to embodiments of the invention, a method of saccharification exhibits at least one of an increased saccharification rate, higher catalytic activity at an acidic pH below 4.5, and higher catalytic activity at a temperature of up to 64° C. as compared to the method performed with the parental pullulanase.

Any amylase can be used in a method of saccharification in view of the present disclosure. As used herein, "amylase" and "amylase enzymes" refer to glycoside hydrolases that hydrolyze $\alpha$-1,4-glucosidic bonds. Examples of amylases include, but are not limited to, glucoamylase, $\alpha$-amylase, and $\beta$-amylase. Preferably, the amylase is glucoamylase.

The use of a truncated pullulanase according to the invention in combination with a glucoamylase in a saccharification reaction has the advantage of providing higher purity glucose and maltose syrups from starch. Additionally, such saccharification reactions allow for the use of reduced concentrations of substrate, higher conversion rates, and can also be conducted at higher temperatures and/or at acidic pH values with higher catalytic activity, consistent with the conditions often used in industrial processes for breaking down starch.

A method of saccharification and/or a method of hydrolyzing $\alpha$-1,6-glucosidic linkages can be performed at any temperature and pH suitable for hydrolysis of $\alpha$-1,6-glucosidic bonds by a truncated pullulanase of the invention. For example, the saccharification reaction can be performed at elevated temperatures of between 60° C. to 64° C., such as 60° C., 61° C., 62° C., 63° C. or 64° C. The saccharification and hydrolysis reactions can also be performed at acidic pH values in a range of 4.0 to 5.5, such as, for example, pH 4.0, 4.1, 4.2, 4.3, 4.4, 4.5, 5.0, or 5.5.

In one particular embodiment, the condition for saccharification comprises a pH of 4.0

In another particular embodiment, the condition for saccharification comprises a temperature of 60° C.

In yet another particular embodiment, the condition for saccharification comprises a pH of 4.5 or below and a temperature of 60° C. to 64° C.

According to embodiments of the invention, a saccharification reaction performed with a truncated pullulanase of the invention exhibits at least one of an increased saccharification rate, a higher catalytic activity at acidic pH, and a higher catalytic activity at temperatures above 60° C. as compared to the same reaction performed with the corresponding parental pullulanase. Preferably, the saccharification reaction exhibits an increased catalytic rate of hydrolysis of $\alpha$-1,6-glucosidic bonds at a pH value below 4.5 and/or at a temperature between 60° C. and 64° C.

The invention also relates to compositions comprising a glucoamylase and an isolated or purified truncated pullulanase comprising a deletion of 94 to 115 amino acids from the amino terminus of a parental pullulanase, wherein the parental pullulanase comprises the amino acid sequence of SEQ ID NO: 2 or SEQ ID NO: 4.

According to embodiments of the invention, the composition can comprise any of the truncated pullulanases of the invention as described herein. In preferred embodiments, the composition comprises a truncated pullulanase comprising a deletion of amino acid residues 1 to 94, 1 to 102, or 1 to 104 from the amino terminus of the parental pullulanase, wherein the parental pullulanase comprises the amino acid sequence of SEQ ID NO: 2 or SEQ ID NO: 4. In particularly preferred embodiments, the composition comprises a truncated pullulanase consisting of SEQ ID NO: 6, SEQ ID NO: 8, or SEQ ID NO: 9.

According to embodiments of the invention, a composition comprising a truncated pullulanase of the invention and a glucoamylase can be used in any of the methods of saccharification described herein.

In yet another general aspect, the invention relates to a system for catalyzing saccharification of a carbohydrate having one or more $\alpha$-1,6-glucosidic linkages, comprising the carbohydrate, a glucoamylase, and an isolated or purified truncated pullulanase comprising a deletion of 94 to 115 amino acids from the amino terminus of a parental pullulanase under a condition suitable for the saccharification, wherein the condition comprises at least one of a pH of 4.5 or less and a temperature of 60° C. or higher, wherein the parental pullulanase comprises the amino acid sequence of SEQ ID NO: 2 or SEQ ID NO: 4.

Any of the truncated pullulanases described herein can be used with a system of the invention. Any of the conditions suitable for the saccharification can be used with a system of the invention.

In a particular embodiment of the system, the truncated pullulanase consists of an amino acid sequence of SEQ ID NO: 6, SEQ ID NO: 8, and SEQ ID NO: 9.

In another particular embodiment of the system, the condition suitable for the saccharification comprises a pH of 4.0.

In another particular embodiment of the system, the condition suitable for the saccharification comprises a temperature of 60° C.

In yet another particular embodiment of the system, the condition suitable for the saccharification comprises a pH of 4.5 or below, and a temperature of 60° C. to 64° C.

In yet another general aspect, the invention provides expression vectors comprising a synthetic polynucleotide encoding a truncated pullulanase according to the invention, and recombinant host cells comprising such expression vectors. Expression vectors according to the invention can comprise a synthetic polynucleotide encoding any of the truncated pullulanases described herein. The expression vectors can also have the capacity to be integrated into a chromosome of a host cell. According to particular embodiments of the invention, an expression vector comprises a synthetic polynucleotide having SEQ ID NO: 5 or SEQ ID NO: 7.

Expression vectors according to the invention can further comprise a native or synthetic promoter sequence, a native or synthetic ribosome binding site, and a native or synthetic termination sequence. These genetic elements can also form part of an expression cassette together with the synthetic polynucleotide sequence encoding a truncated pullulanase enzyme according to the invention, with such expression cassette forming part of an expression vector. For example, an expression vector can comprise an expression cassette containing the following elements: a promoter sequence, a synthetic ribosome binding site, a synthetic polynucleotide encoding a truncated pullulanase of the invention, and a synthetic termination sequence. A signal sequence directing secretion of the expressed truncated pullulanase can also be included in the expression vector or expression cassette, and is preferably inserted upstream of the start codon of the polynucleotide encoding the truncated pullulanase. Preferably, an expression vector comprises a signal sequence that directs secretion of the truncated pullulanase.

According to preferred embodiments of the invention, the expression vectors are compatible with expression in bacterial host cells, preferably *Bacillus* strains, and more preferably *Bacillus subtilis*. In particularly preferred embodiments, the expression vectors are capable of being integrated in a chromosome of a *Bacillus* strain, and more preferably *Bacillus subtilis*. Expression vectors that can be used to integrate a polynucleotide sequence into a chromosome of a host cell, and methods of constructing such expression vectors, are well known to one of ordinary skill in the art in view of the present disclosure.

According to embodiments of the invention, a recombinant host cell can be genetically engineered to comprise one or more synthetic polynucleotide sequences encoding a truncated pullulanase of the invention. Any method known in the art can be used to genetically engineer a host cell to comprise one or more synthetic polynucleotide sequences encoding a truncated pullulanase enzyme according to the invention, such as, for example, chromosomal integration. Vectors that can be used in an integration step are well known in the art (Sueharu et al., 1992), and preferably contain a temperature sensitive origin and a selection marker. Such vectors provide for selective integration into a chromosome of the host cell at a designated locus by a Campbell-type mechanism, after which the selection marker of the plasmid is removed by a homologous recombination step during a subsequent incubation period.

According to embodiments of the invention, a recombinant host cell can be a modified recombinant host cell that has been genetically engineered to inactivate endogenous proteins. Endogenous proteins that can be inactivated in the modified host cell include, but are not limited to, extracellular proteases and proteins that affect spore formation in a spore forming bacteria. The recombinant host cell can be modified to inactivate endogenous proteins prior to introducing one more synthetic polynucleotides encoding a truncated pullulanase of the invention into the host cell, or after introduction of the one more synthetic polynucleotides encoding a truncated pullulanase of the invention into the host cell. Preferably, the recombinant host cell is modified to inactivate endogenous proteins prior to introduction of the one more synthetic polynucleotides encoding a truncated pullulanase of the invention into the host cell.

In a preferred embodiment, a recombinant host cell is a *Bacillus subtilis* cell that has been previously engineered to inactivate a few endogenous proteins. In particular, the *Bacillus subtilis* strain can be engineered to inactivate extracellular proteases, such as subtilisin (AprE) and neutral metalloproteaseE (NprE). The *Bacillus subtilis* strain can also be engineered to inactivate proteins that play a role in spore formation, such as sporulation-specific sigma-F factor encoded by the spoIIAC gene. Such genetically engineered *Bacillus subtilis* strains have the advantage of providing for improved expression and secretion of the expressed pullulanase enzymes.

In yet another general aspect, the invention provides a method of producing a truncated pullulanase according to the invention. According to embodiments of the invention, the method comprises growing a recombinant host cell comprising a polynucleotide sequence encoding a truncated pullulanase of the invention under conditions suitable for expression of the truncated pullulanase, and obtaining the truncated pullulanase from the recombinant host cell or its supernatant.

Any of the recombinant host cells described herein can be used in a method of producing a truncated pullulanase according to the invention. Recombinant host cells comprising at least one synthetic polynucleotide sequence encoding a truncated pullulanase according to the invention can be expressed and cultured under any culture conditions suitable for expression of the truncated pullulanase. Truncated pullulanases secreted from the recombinant host cells can be recovered from the cell culture, including from the recombinant host cell or its supernatant, by any method known in the art, including but not limited to filtration, centrifugation, etc.

According to embodiments of the invention, high yield production of truncated pullulanases of the invention can be achieved by fermentation of an engineered *Bacillus subtilis* integrated with a genetic construct comprising a synthetic polynucleotide encoding a truncated pullulanase. Preferably, the *Bacillus subtilis* strain used is devoid of antibiotic resistant genes, and is thus environmentally friendly and suitable for the production of truncated pullulanases that can be used for the commercial preparation of glucose or maltose for the food industry.

Without wishing to be bound by any theories, it is believed that the first 111 amino acids beginning at the N-terminus of the mature pullulanase from *Bacillus acidopullulyticus* are disordered based on analysis of the crystal structure (Turkenburg, Brzozowski et al. 2009). This observation of a poorly defined structure of the N-terminus of mature pullulanase protein suggests that this enzyme may tolerate the removal of N-terminal residues without any impairment of the native three-dimensional structure, possibly leading to better conformational stability and higher enzymatic activity. Again without wishing to be bound by any theories, it is believed that structural perturbation by terminal truncation could be a fast, efficient, and highly effective way to explore the potential improvement of the protein thermal stability and the enzyme catalytic activity without the need for conducting a selection at elevated temperatures. The truncated form of the enzyme may also have the advantages of a lower molecular weight and potentially higher specific catalytic activity over the native pullulanase obtainable from or produced by a microorganism in the saccharification of starch, which would be useful in the starch industry. Thus, based on the implication from the crystal structure of the mature pullulanase from *Bacillus acidopullulyticus*, it is believed that this enzyme may potentially tolerate the removal of N-terminal amino acid residues for the reasons described above.

The following examples of the invention are to further illustrate the nature of the invention. It should be understood that the following examples do not limit the invention and that the scope of the invention is to be determined by the appended claims.

EXAMPLES

Example 1: Construction of the Plasmid pYF-tsDE pYF-tsDE (see FIG.), a temperature-sensitive plasmid, is an *E. coli/B. subtilis* shuttle plasmid. The pYF-tsDE plasmid comprises a temperature-sensitive origin of replication that is active at 30° C., and an erythromycin determinant gene (ErmC) resistant to 300 µm/mL of erythromycin in *E. coli*, and 5 µg/mL of erythromycin in *B. subtilis* (Sueharu et al 1992). At 37° C., the nonpermissive temperature, the origin of replication is deactivated and the plasmid is integrated into the host cell chromosome at the designated locus for the ErmC gene selection.

Figure 2:
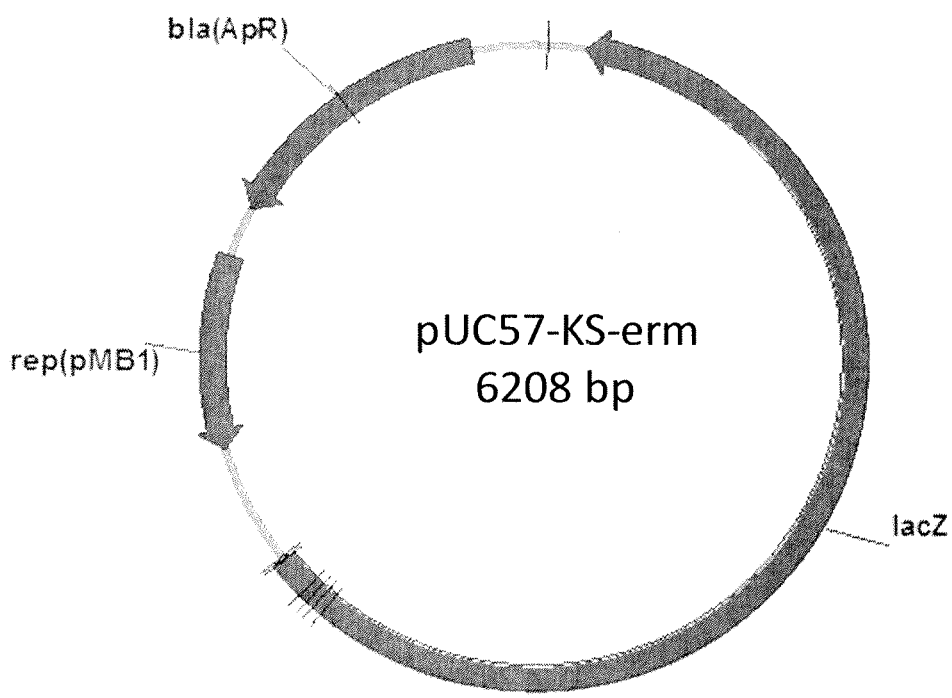
FIG. 2 is a schematic representation of a pUC57-KS-erm vector from which a pYF-tsDE vector can be obtained according to an embodiment of the invention.

The construction of the plasmid pYF-tsDE is described as follows. pUC57-KS-erm (provided by GenScript, FIG. 2) was double-digested with BglII. The 3.8 kbp fragment produced from the enzymatic digestion was purified and re-ligated using T4 ligase (New England Biolabs). The cloned plasmid was denoted as pYF-tsDE. It was propagated in *E. coli* TOP10 cells, and was used as the backbone for all of the following genetic manipulations.

Example 2: Construction of the Protease-Deficient *B. Subtilis* Strain

The use of genetically engineered bacilli as host cells for the production of recombinant enzymes is well established (Widner et al., 2000). These recombinant host cells generally comprise one or more nucleic acid constructs encoding target enzyme sequences for expression. In the invention, *B. subtilis* was chosen as the recipient strain for gene manipulations. The transformation of *Bacillus* strains with a nucleic acid construct can be achieved by well-known methods in the art, such as with competent cells, electroporation or protoplast transformation (Young and Spizizen 1961; Shigekawa and Dower 1988; Chang and Cohen 1979).

In the invention, a single pullulanase enzyme expression cassette was designed that typically comprises native or synthetic promoter sequences, a signal sequence selected from bacilli for efficient export, a synthetic ribosome binding site, a pullulanase coding gene from *Bacillus deramificans*, and a synthetic transcription terminator. This arrangement substantially enhances the gene expression level and pullulanase secretion in the host strains. The genetic exchange of the gene encoding the pullulanase enzyme into the designated locus on the chromosome of the *Bacillus* cells can be done by plasmid-mediated single-crossover homologous recombination.

Extracellular protease activities can be detrimental to heterogeneous enzyme secretion in bacilli. It has been shown that the two major extracellular proteases, subtilisin E (AprE) and neutral metalloproteaseE (NprE), contribute to over 85% of the extracellular protease activity in bacilli. Moreover, spore-forming bacilli can form dormant cells during fermentation that exponentially decreases the production efficiency. The spoIIAC gene encoding sporulation-specific sigma-F factor plays a crucial role in directing the specificity of RNA polymerase transcription, and the gene expression product of spoIIAC is required for spore formation.

Thus, in the invention the three aforementioned genes have been inactivated in a sequential manner by a single crossover Campbell-type mechanism in order to obtain structural integrity of pullulanase gene expression. Briefly, pYF-tsDE (obtained as described in Example 1) was digested with BglII and treated with calf intestinal alkaline phosphatase (CIP) to inhibit religation. In order to obtain each gene deletion, approximately 500 base pairs of homologous regions flanking the gene to be deleted were amplified by PCR from the genomic DNA. Isolated colonies of *Bacillus subtilis* were heated at 98° C. for 5 minutes, and served directly as the genomic DNA template for PCR reactions. The primers shown below (SEQ ID NOs: 13-24) were synthesized by GenScript and used for PCR to amplify the flanking sequences of the Apr, Npr and SpoIIAC genes of *Bacillus subtilis*, respectively:

```
pksb-apr_czF1
GGTATCGATAAGCTTCCTGCAGATCTCTCAGGAGCATTTAACCT pksb-apr_R1
GCACCTACTGCAATAGTAAGGAACAGATTGCGCAT pksb-apr_F2
ATGCGCAATCTGTTCCITACTATTGCAGTAGGTGC pksb-apr_czR2
AATATGGCGGCCGCGAATTCAGATCTCTAATGCTGTCTCGCGTT pksb-npr_czF1
GCITATCGATAAGCTTCCTGCAGATCTCATCTTCCCCTTGAT pksb-npr_R1
CAGTCTTCTGTATCGTTACGCTTTTAATTCGGCT pksb-npr_F2
AGCCGAATTAAAAGCGTAACGATACAGAAGACTG pksb-npr_czR2
TATGGCGGCCGCGAATTCAGATCTCCTGGCCAGGAGAATCT pksb-spo_czF1
GGTATCGATAAGCTTCCTGCAGGAACAATCTGAACAGCAGGCACTC pksb-spo_R1
TTGTCAAACCATTTTTCTTCGCCCGATGCAGCCGATCTG pksb-spo_F2
CAGATCGGCTGCATCGGGCGAAGAAAAATGGTTTGACAA pksb-spo_czR2
ATATGGCGGCCGCGAATTCAGATCTGTTCATGATGGCAAGACAC
```

Amplification reactions were typically performed in a total volume of 50 µL as follows: initial denaturation at 98° C. for 8 minutes, followed by 25 to 30 cycles (96° C. for 15 seconds, 58° C. for 15 seconds, and 72° C. for 30 seconds), and the reaction was finalized at 72° C. for 2 minutes. The amplification products were identified by 0.8% agarose gels and purl tied.

An internal deleted version of each gene was constructed by splice overlap extension PCR (SOE) as follows: The purified upstream and downstream sequences of each gene from separate PCR reactions were mixed together at a 1:1 molar ratio to serve as the amplification template. The primers labeled XX-CZ-F1 and XX-CZ-R2 were used to produce the spliced fragment of each gene. The fragment was subsequently cloned into the linearized pYF-tsDE vector at the BglII site by the Clone-EZ cloning kit from GenScript. The constructed temperature-sensitive plasmids typically contained an internal deletion of 400-500 base pairs as compared to the corresponding intact genes. These recombinant plasmids Were denoted as pYF-tsDE-Apr, pYF-tsDE-Npr, and pYF-tsDE-SpoII, respectively.

Different allelic exchanges of intact genes with the original chromosomal genes were achieved by single crossover homologous recombination. The corresponding deletion plasmid was transformed into competent *Bacillus* cells by the modified method described by Young (Young and Spizizen 1961). A single transformant selected from plates supplemented with erythromycin at the permissive temperature of 30° C. was streaked onto another erythromycin containing plate, and incubated at the nonpermissive temperature of 37° C. for selection of the transformants with the temperature-sensitive plasmid integrated into the host chromosome. To obtain the gene replacement at the designated locus, several colonies selected from plates were transferred into 2YT media and incubated at 30° C. for 5-7 days (fresh 2YT media was exchanged every two days). Erythromycin sensitive *Bacillus* cells were screened by PCR for plasmid excision and allelic gene replacement (see SEQ ID NOs: 9, 10 and 11). The protease-deficient phenotypes were further confirmed by the shrunken halos on LB plates supplemented with 1.0% nonfat dry milk.

Example 3: Construction of Pullulanase-Producing *Bacillus* Strains

The integration plasmid was constructed using pYF-tsDE essentially the same way as described above. In order to integrate the expression cassette into the designated AmyE locus of the chromosome, a pullulanase expression cassette was flanked by 800-base pair homologous regions of upstream and downstream sequences of the AmyE locus of the chromosome. A few head to tail native selected bacterial chromosomal DNA fragments and functional synthetic sequences required for controlling the expression of the pullulanase gene were assembled.

A typical pullulanase expression cassette contained the following components: a native or synthetic promoter sequence, a synthetic ribosome binding site, a truncated pullulanase coding gene derived from *Bacillus deramificans* and a synthetic termination sequence. These sequences were synthesized and operably assembled together by GenScript. A strong native signal sequence selected from *Bacillus subtilis* that provides for efficient secretion of the enzyme expressed from the downstream coding region was inserted upstream of the start codon of the pullulanase coding gene. The entire pullulanase expression cassette was inserted into the linearized pYF-tsDE at the BglII site by the Clone-EZ cloning kit from GenScript. The resulting temperature sensitive integration plasmid was denoted as pYF-tsINT-puI and introduced into the competent protease deficient, sporulation-disabled *Bacillus subtilis* strain.

The marker-free gene replacement of AmyE with the pullulanase expression cassette was performed essentially the same way as described above. The halo formation on the red-pullulan plates confirmed the successful integration of the pullulanase coding gene into the chromosome of *Bacillus subtilis*. PCR reactions further confirmed that the expression cassette was indeed present at the AmyE locus of the recipient strain.

The engineered pullulanase-producing strains were stored at −80° C.

Example 4: Pullulanase Production in a Shake-Flask Process

Figure 3:
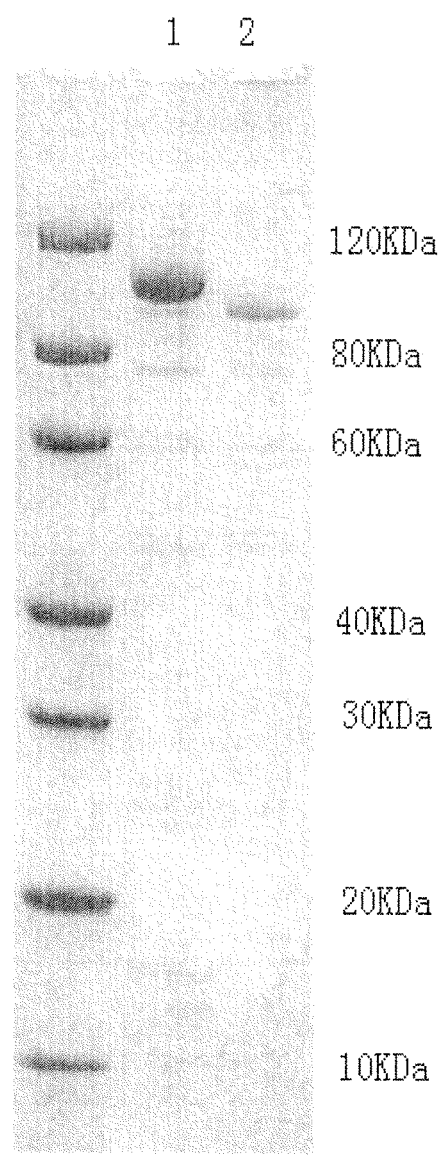
FIG. 3 is an image of an SDS-PAGE gel showing the size comparison of a parental pullulanase (SEQ ID NO: 4) (lane 1) with a corresponding truncated pullulanase (SEQ ID NO: 8) (lane 2) comprising a deletion of amino acid residues 1-104 at the N-terminus of the parental pullulanase.

A single fresh *Bacillus subtilis* colony containing the pullulanase expression cassette was grown for 16 hours to mid-log phase in 20 mL of media containing 4.0% maltose syrup, 2.0% peptone, 0.1% yeast extract, and 0.6% $KH_2PO_4$. 1.2 mL of the grown culture was then inoculated into 30 mL of media containing 12.0% maltose syrup, 1.0% peptone, 1.0% yeast extract, 0.2% $KH_2PO_4$, and 0.003% $MnCl_2$, and incubated at 120 strokes per minute in a reciprocal shaker for 3 days. Samples (1 mL) were taken after 24 hours, 48 hours, and 72 hours, and centrifuged at 10000 g for 1 minute. The supernatants were saved for SDS-PAGE analysis, and the parental and truncated pullulanase enzymes were run on 8-16% SDS-PAGE in lanes 1 and 2, respectively, as shown in FIG. 3. The truncated pullulanase enzyme (SEQ ID NO: 8) comprises a deletion of amino acid residues 1 to 104 at the N-terminus of the parental pullulanase enzyme (SEQ ID NO: 4), with the deletion starting from the amino terminus of the parental pullulanase. The SDS-PAGE analysis indicated that both proteins were obtained in high purity. As expected, the apparent molecular weight of parental pullulanase was approximately 100 kD and that of truncated form was approximately 86 kD.

Assays to test for pullulanase activity were performed using the method described below in Example 6.

Example 5: Pullulanase Production in a Fed-Batch Fermentation Process

Frozen engineered *Bacillus* strain stored at −80° C. obtained as described in Example 3 was streaked on agar slants and incubated overnight at 37° C. The agar slants were prepared as follows: 1.0% Tryptone, 0.5% yeast extract, 1.0% NaCl, and 2.0% Bacto-agar (Difco).

Several fresh colonies were suspended in a seed flask containing 50 mL of the following contents: 4.0% maltose syrup, 2.0% peptone, 0.1% yeast extract, and 0.6% $KH_2PO_4$. After incubation at 37° C. for 16 hours, the whole volume was transferred to a 7 L stainless steel pilot fermenter containing 4 L of media having the following composition: 6.0% maltose syrup, 1.0% peptone, 1.0% yeast extract, 0.2% $KH_2PO_4$ and 0.003% $MnCl_2$. Cultivation was performed at 37° C. with the agitator speed set at 140 g. The aeration rate was adjusted to 650 L/H after continuous fermentation for 6 hours. The cultivation pH was then controlled to be 5.7±0.2 with 5.0% phosphoric acid. A sterile medium of a defined composition (48% maltose syrup, 6.0% peptone, 8.0% yeast extract) was fed continuously to the culture at the rate of 0.5 L/18 hours for the first 18 hours and at the rate of 1 L/18 hours for the rest of the feeding. The fermentation was terminated after about 29 hours of feeding. The entire broth from the fermenter was collected and centrifuged at 8000 g at 4° C. for 30 minutes, and the supernatant was assayed for pullulanase activity.

Example 6: Measurement of Pullulanase Activity

Pullulanase activity is measured in Bestzyme Pullulanase Units (BPU). One BPU is defined as the quantity of enzyme that will produce 360 μg of reducing sugar (calculated as glucose) from pullulan per minute under conditions of 60° C. and pH 4.5.

Briefly, 1 mL of properly diluted samples of pullulanase enzyme mixed with 1 mL of 0.5% pullulan was incubated at 60° C. for 30 minutes. Then, 3 mL of 3.5-dinitrosalicylic acid (DNS) solution were added and the sample was boiled for 7 minutes. The sample was cooled, and then water (10 mL) was added and mixed. The reducing sugar generated was determined by the Somogyi-Nelson method (Somogyi et al, 1944).

Example 7: Formulations and Applications of Truncated Pullulanase Enzymes

The results shown below are based on the truncated pullulanases shown in SEQ ID NO: 6 and SEQ ID NO: 8, referred to hereinafter as "Td-A" and "Td-D," respectively. These truncated pullulanases comprise either a deletion of amino acid residues 1 to 94, or a deletion of amino acid residues 1 to 104 from the amino terminus of the parental pullulanase shown in SEQ ID NO: 4.

Unless defined otherwise, the unit definitions used are as follows:

BGU: the activity of glucoamylase is measured in Bestzyme Glucoamylase Units. One BGU is defined as the quantity of enzyme that produces 200 mg of glucose from soluble starch per hour under conditions of 40° C. and pH 4.6.

BPU: the activity of pullulanase is measured in Bestzyme Pullulanase Units. One BPU is defined as the quantity of enzyme that will release 360 µg of glucose equivalent reducing sugar from pullulan per minute under conditions of 60° C. and pH 4.5.

gDS: Grams of Dry Solid

The pullulanase enzyme expressed and isolated from *Bacillus subtilis* cells was first tested for saccharification using a corn maltodextrin solution, which was made at 31% dry solids (DS) and mixed well. The pH was then adjusted to pH 4.3 using HCl. Reactions were performed in a 200 mL reaction volume. The pullulanase was added at doses of 0.300, 0.250 and 0.150 BPU/gDS, respectively, from a diluted stock solution made with tap water to the solution of glucoamylase (fixed concentration at 0.225 BGU/gDS). The parental pullulanase (0.300 BPU/gDS) was added to another flask as the control. The reactions were held at 60° C. for 24, 40, and 48 hours, respectively. The samples were then collected and filtered through a 0.22 µm membrane and enzyme-inactivated by heating up to 100° C. for HPLC analysis. The results are summarized in Table 1 below.

TABLE 1

Glucose Yield Obtained from Saccharification Reactions with Truncated Pullulanase Enzyme and the Corresponding Parental Pullulanase Enzyme at pH 4.3

| Glucoamylase | Pullulanase | | Glucose % | | |
|---|---|---|---|---|---|
| dosage BGU/gDS | dosage | BPU/gDS | 24 hours | 40 hours | 48 hours |
| 0.225 | — | — | 90.9 | 94.1 | 94.7 |
| 0.225 | Parental | 0.300 | 94.5 | 96.3 | 96.4 |
| 0.225 | Td-A | 0.300 | 95.7 | 96.5 | 96.5 |
| 0.225 | Td-D | 0.300 | 95.6 | 96.4 | 96.4 |
| 0.225 | Td-D | 0.250 | 95.2 | 96.4 | 96.4 |
| 0.225 | Td-D | 0.200 | 94.7 | 96.2 | 96.3 |
| 0.225 | Td-D | 0.150 | 94.6 | 96.1 | 96.2 |

From the results, it can be seen that the glucose yield of the parental enzyme at 24 hours with a dose of 0.300 BPU/gDS (94.5%) was greater than the glucose yield obtained from the process with glucoamylase alone (90.9%), confirming the positive impact of including a pullulanase enzyme in the saccharification process. The truncated enzymes maintained or even increased the glucose yield (95.6%-96.5%) as compared to the glucose yield of parental enzyme (94.5%-96.4%) at the same dose of enzyme (0.300 BPU/gDS), demonstrating that pullulanase enzymes can tolerate the removal of N-terminal residues without impairing enzymatic activity. Importantly, during the first 24-hour reaction time, the truncated pullulanase was able to maintain similar glucose yields as dose decreased (down to 0.150 BPU/gDS), and sustained activity for an extended reaction time of up to 48 hours. Furthermore, the rate of saccharification catalyzed by the truncated pullulanase enzyme was faster than that of the parental enzyme during the first 24-hour reaction time (data not shown). Taken together, these findings suggest that the removal of N-terminal residues of the pullulanase, with the deletion beginning from the first amino acid residue at the N-terminus, leads to better conformational stability and higher enzymatic activity.

Next, the pH tolerance of the truncated pullulanase enzymes was tested by carrying out the saccharification process at a lower pH. In particular, the saccharification reactions were carried out at as described above, except at a pH value of 4.0. The results are shown below in Table 2.

TABLE 2

Glucose Yield Obtained from Saccharification Reactions with Truncated Pullulanase Enzyme and the Corresponding Parental Pullulanase Enzyme at pH 4.0

| Glucoamylase | Pullulanase | | Glucose % | | |
|---|---|---|---|---|---|
| dosage BGU/gDS | dosage | BPU/gDS | 24 hours | 40 hours | 48 hours |
| 0.225 | — | — | 90.9 | 94.1 | 94.7 |
| 0.225 | Parental | 0.300 | 92.8 | 95.4 | 95.9 |
| 0.225 | Td-A | 0.300 | 95.8 | 96.5 | 96.5 |
| 0.225 | Td-D | 0.300 | 95.6 | 96.4 | 96.5 |

As shown by the results in Table 2, at pH 4.0, the glucose yield from the saccharification reaction catalyzed by the truncated pullulanase enzymes (95.8% and 95.6%) was higher than that of the parental enzyme (92.8%) during the first 24-hour reaction time, and was sustained for up to 48-hours. Notably, the parental pullulanase failed to reach the minimal percentage of the glucose yield required by the starch industry (96%), even with the extended reaction time of up to 48 hours. In contrast, the truncated pullulanase enzymes showed enhanced catalytic activity at the acidic pH condition of 4.0. The final glucose yields of 96.5% and 96.4% obtained with the truncated pullulanase enzyme were reached at a 40-hour reaction time (Table 2). Similar results were obtained from multiple experiments (data not shown).

Additionally, the thermal stability and thermal activity of the truncated pullulanase enzymes were tested. Saccharification reactions were carried out at 60° C., 62° C., and 64° C., respectively, which are temperatures often used in the starch industry. The results are shown below in Table 3.

TABLE 3

Glucose Yield Obtained from Saccharification Reactions with Truncated Pullulanase Enzyme and the Corresponding Parental Pullulanase Enzyme at Various Temperatures

| T° C. | Glucoamylase dosage BGU/gDS | Pullulanase | dosage BPU/gDS | Glucose % | | |
|---|---|---|---|---|---|---|
| | | | | 24 hours | 40 hours | 48 hours |
| 60 | 0.225 | Parental | 0.300 | 94.5 | 96.3 | 96.4 |
| 62 | | | | 94.6 | 96.2 | 96.3 |
| 64 | | | | 93.4 | 95.4 | 95.7 |
| 60 | 0.225 | Td-A | 0.300 | 95.5 | 96.5 | 96.5 |
| 62 | | | | 95.5 | 96.4 | 96.4 |
| 64 | | | | 94.4 | 95.9 | 96.0 |
| 60 | 0.225 | Td-D | 0.300 | 95.6 | 96.4 | 96.5 |
| 62 | | | | 95.6 | 96.3 | 96.4 |
| 64 | | | | 95.6 | 96.1 | 96.1 |

As expected, the parental pullulanase had a decreased ability to catalyze the saccharification reaction during the first 24-hour reaction time period at the higher temperature of 64° C. (Table 3). In contrast, the truncated pullulanases retained significantly high catalytic ability even at temperatures up to 64° C., indicating that a positive impact on the thermal stability and thermal activity is achieved by N-terminal truncation of the parental pullulanase enzyme (Table 3).

A third truncated pullulanase was expressed and isolated from *Bacillus subtilis* cells, and the activity of this third truncated pullulanase was compared to that of the two truncated pullulanase enzymes characterized above, but under harsher testing conditions. This third truncated pullulanase, referred to as "Td-C", is shown in SEQ ID NO: 9, and has a deletion of amino acid residues 1-102 from the amino terminus of the parental pullulanase enzyme shown in SEQ ID NO:4.

A harsher testing condition was applied as follows: a corn maltodextrin solution at 32% dry solids (DS) was mixed well and pH adjusted to 4.0 using HCl. Reactions were performed in a 200 mL reaction volume. The truncated pullulanases (Td-C, Td-A and Td-D) were added to a solution of glucoamylase at a dose of 0.270 BPU/gDS from a diluted stock solution made with tap water. The concentration of glucoamylase in the solution as fixed at 0.225 BGU/gDS. The reactions were held at 60° C. for 24, 40 and 48 hours, respectively. The samples were then collected and filtered through a 0.22 μm membrane and enzyme-inactivated by heating up to 100° C. for HPLC analysis. The results are summarized in Table 4 below.

TABLE 4

Glucose Yield Obtained from Saccharification Reactions with Truncated Pullulanase Enzymes at pH 4.0

| Glucoamylase dosage BGU/gDS | Pullulanase | dosage BPU/gDS | Glucose % | | |
|---|---|---|---|---|---|
| | | | 24 hours | 40 hours | 48 hours |
| 0.225 | Td-C | 0.270 | 94.9 | 96.2 | 96.2 |
| 0.225 | Td-A | 0.270 | 95.4 | 96.2 | 96.2 |
| 0.225 | Td-D | 0.270 | 95.1 | 96.2 | 96.2 |

As shown by the results in Table 4, under the harsher conditions, similar glucose yield from the saccharification reactions catalyzed by each of the truncated pullulanases was achieved at the end of the 40-hour reaction time period. In the first 24-hour reaction time period, the truncated pullulanases Td-A and Td-D showed slightly faster saccharification rates and slightly better glucose yields (95.4% and 95.1%) than the truncated pullulanase Td-C (94.9%). However, the glucose yields of all three truncated pullulanase enzymes tested are comparable.

Taken together, the above results demonstrate that truncated pullulanase enzymes of the invention have advantageous properties that are desirable to glucose manufacturers seeking to perform saccharification reactions for shorter reaction time periods (e.g., 36 hours or less), and at lower pH or higher temperature conditions, without sacrificing glucose yield. In particular, the results demonstrate that truncated pullulanases of the invention have improved stability at pH values below pH 4.5, including down to pH 4.0, and improved stability at increased temperatures between 60° C. and 64° C. as compared to the stability of the parental pullulanase under the same temperature and pH conditions.

Moreover, truncated pullulanases having a decreased molecular weight have an advantage of higher specific activity (activity/unit weight). Therefore, these truncated pullulanase enzymes can be used in saccharification processes at lower amounts in terms of weight without sacrificing activity. In other words, the invention provides lower molecular weight pullulanases having equivalent, if not improved activity in catalyzing hydrolysis of α-1,4-glucosidic linkages, which make the truncated pullulanases of the invention particularly advantageous for use in the starch industry.

Lastly, the performance of the truncated pullulanase enzyme in a saccharification reaction with an enzyme composition containing barley β-amylase (Genencor, 1230 DP/gDS) was also tested, which is an important application of pullulanases in the maltose production industry. Briefly, a maltodextrin solution, which was made at 31% dry solids (DS), was mixed well and then pH adjusted to 5.2 using HCl. The pullulanase and β-amylase enzymes were added to the maltodextrin solution (200 mL) at a dose of 1.000 BPU/gDS and 1.23 DP/gDS, respectively. The β-amylase (1.23 DP/gDS) was added alone to another flask containing maltodextrin (32% DS, 200 mL) as the control. The 200 mL reaction volume was held at 60° C. for 24 hours. The samples were then collected and filtered through a 0.22 μm membrane and enzyme-inactivated by heating up to 100° C. for 15 minutes followed by HPLC analysis. The results are shown below in Table 5.

TABLE 5

Maltose Yield of the Truncated and Parental Pullulanases for the Maltose Production

| β-amylase dosage DP/gDS | Pullulanase | dosage BPU/gDS | Maltose % |
|---|---|---|---|
| 1.23 | — | — | 61.9 |
| 1.23 | Parental | 1.000 | 73.3 |
| 1.23 | Td-A | 1.000 | 75.2 |
| 1.23 | Td-D | 1.000 | 75.9 |

As shown by the results in Table 5, compared to the parental pullulanase, the truncated pullulanases exhibited better performance under the same reaction conditions. As expected, the maltose yield from the process with the parental enzyme (73.3%) was higher than that from the process with β-amylase alone (61.9%). The truncated pullulanases provided significantly higher maltose yield (75.9%) than the parental pullulanase, indicating that the truncated form has improved catalytic activity.

Collectively, the results of the above experiments indicate that truncated pullulanases according to the invention have increased pH tolerance, increased thermal stability, and increased thermal activity as compared to the parental enzyme. Therefore, truncated pullulanase enzymes of the invention have potential for use in saccharification processes of carbohydrates, and particularly for use in the starch industry.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES (1) Bakshi, A., Patnaik, P. R. and Gupta, J. K. (1992) "Thermostable Pullulanase from a Masophilic *Bacillus Cereus* Isolate and its Mutant UV7.4."*Biotechnol. Lett.* 14:689-694.
(2) Chang, S. and Cohen, S. N. (1979). "High Frequency Transformation of *Bacillus Subtilis* Protoplasts by Plasmid DNA."*Mol. Gen. Genet.* 168:111-115.
(3) d'Enfert, C., Ryter. A., et al. (1987). "Cloning and Expression in *Escherichia Coli* of the *Klebsiella pneumoniae* Genes for Production, Surface Localization and Secretion of the Lipoprotein Pullulanase." *EMBO J.* 6: 3531-3538.

(4) Horinouchi, S. and Weisblum B. (1982). "Nucleotide Sequence and Functional Map of Pe194. A Plasmid That Specifies Inducible Resistance to Macrolide, Lincosamide, and Strep to Gramin Type B Antibodies" *J. Bacteria* 150: 804-814.

(5) Koch, R., Canganella, F., et al. (1997). "Purification and Properties of a Thermostable Pullulanase from a Newly Isolated *Thermophilicanaerobic Bacterium, Fervidobacterium pennavorans* Ven5." *Appl. Environ. Microbiol* 63: 1088-1094.

(6) Kusano, S., Nagahata, N., Takahashi, S., Fujimoto, D. and Sakano, Y (1988). "Purification and Properties of *Bacillus acidopullulyticus* Pullulanase." *Agric. Biol. Chem.* 52: 2293-2298.

(7) Lappalainen, A., Niku-Paavola, M.-L., Suortti, T., and Poutanen, K. (1991). "Purification and Characterization of *Bacillus acidopullulyticus* Pullulanase for Enzymatic Starch Modification." *Starch* 43: 477-482.

(8) Nakamura, N., Watanabe, K., et al. (1975). "Purification and Some Properties of Alkaline Pullulanase from a Strain of *Bacillus* No. 202-1, an Alkalophilic Microorganism."*Biochim. Biophys. Acta* 397: 188-193.

(9) Nelson N. (1944). "A Photometric Adaptation of the Somogyi Method for the (10) Determination of Glucose." *J. Biol. Chem.* 153: 375-380.

(11) Norman, B. E. (1982). "A Novel Debranching Enzyme for Application in the Glucose Syrup Industry." *Starch* 34:340-346.

(12) Odibo, F. J. C. and Obi, S. K. C. (1988). "Purification and Characterization of a Thermostable Pullulanase from *Thermoactinomyces thalpophilus."* *J. Industr. Microbiol.* 3:343-350.

(13) Shigekawa, K. and Dower, W. J. (1988). "Electroporation of Eukaryotes and Prokaryotes: A General Approach to the Introduction of Macromolecules into Cells." *Biotechniques* 6: 742-751.

(14) Turkenburg. J. P., Brzozowski, A. M., et al. (2009). "Structure of a Pullulanase from *Bacillus Acidopullulyticus."* *Proteins* 76: 516-519.

(15) Wallenfels, K., Bender, H., et al. (1966). "Pullulanase from Aerobacteraerogenes; Production in a Cell-Bound State. Purification and Properties of the Enzyme." *Biochem. Biophys. Res. Commun.* 22: 254-261.

(16) Widner, B., Thomas, M., Sternberg, D., Lammon, D., Behr, R., and Sloma, A. (2000). "Development of Marker-Free Strains of *Bacillus subtilis* Capable of Secreting High Levels of Industrial Enzymes." *J. Industr. Microbiol. Biotech.* 25: 204-212.

(17) Young, F. E. and Spizizen, J. (1961). "Physiological and Genetic Factors Affecting Transformation of *Bacillus subtilis."* *J. Bacteriol.* 81: 823-829.

We claim:

1. A method of catalyzing saccharification of a carbohydrate having at least one α-1,6-glucosidic linkage, the method comprising contacting the carbohydrate with an isolated or purified truncated pullulanase consisting of the amino acid sequence of SEQ ID NO: 6 under a condition suitable for the saccharification, wherein the condition comprises at least one of a pH of 4.5 or less and a temperature of 60° C. or higher.

2. The method according to claim 1, wherein the condition for saccharification comprises a pH of 4.0.

3. The method according to claim 1, wherein the condition for saccharification comprises a temperature of 60° C.

4. The method according to claim 1, wherein the condition for saccharification comprises a pH of 4.5 or below, and a temperature of 60° C. to 64° C.

5. The method according to claim 1, wherein the carbohydrate is selected from the group consisting of starch, amylopectin, dextran, maltodextrin, pullulan, and glycogen.

6. The method according to claim 1, wherein the method exhibits at least one of an increased saccharification rate, higher catalytic activity at an acidic pH below 4.5, and higher catalytic activity at a temperature of up to 64° C. as compared to the method performed with a pullulanase comprising the amino acid sequence of SEQ ID NO: 4.

7. A method of catalyzing saccharification of a carbohydrate having at least one α-1,6-glucosidic linkage, the method comprising contacting the carbohydrate with a glucoamylase and an isolated or purified truncated pullulanase consisting of the amino acid sequence of SEQ ID NO: 6 under a condition suitable for the saccharification, wherein the condition comprises at least one of a pH of 4.5 or less and a temperature of 60° C. or higher.

8. The method according to claim 7, wherein the condition for saccharification comprises a pH of 4.0.

9. The method according to claim 7, wherein the condition for saccharification comprises a pH of 4.5 or below, and a temperature of 60° C. to 64° C.

10. The method according to claim 7, wherein the carbohydrate is selected from the group consisting of starch, amylopectin, dextran, maltodextrin, pullulan, and glycogen.

11. The method according to claim 7, wherein the method exhibits at least one of an increased saccharification rate, higher catalytic activity at an acidic pH below 4.5, and higher catalytic activity at a temperature of up to 64° C. as compared to the method performed with a pullulanase comprising the amino acid sequence of SEQ ID NO: 4.

12. A system for catalyzing saccharification of a carbohydrate having at least one α-1,6-glucosidic linkage, comprising the carbohydrate, a glucoamylase and an isolated or purified truncated pullulanase consisting of the amino acid sequence of SEQ ID NO: 6.

* * * * *

SEQUENCE LISTING

```
<160> NUMBER OF SEQ ID NOS: 25

<210> SEQ ID NO 1
<211> LENGTH: 2766
<212> TYPE: DNA
<213> ORGANISM: Bacillus acidopullulyticus

<400> SEQUENCE: 1
gattctactt cgactaaagt tattgttcat tatcatcgtt ttgattccaa ctatacgaat      60
tgggacgtct ggatgtggcc ttatcagcct gttaatggta atggagcagc ttaccaattc     120
actggtacaa atgatgattt tggcgctgtt gcagatacgc aagtgcctgg agataataca     180
caagttggtt tgattgttcg taaaaatgat tggagcgaga aaaatacacc aaacgatctc     240
catattgacc ttgcaaaagg ccatgaagta tggattgtac aaggggatcc aactatttat     300
tacaatctga gcgacgcaca ggctgccgca ataccatctg tttcaaatgc ctatcttgat     360
gatgaaaaaa cagtactagc aaagctaagt atgccgatga cgctggcgga tgctgcaagc     420
ggctttacgg ttatagataa aaccacaggt gaaaaaatcc ctgtcacctc tgctgtatcc     480
gcaaatccgg taactgccgt tcttgttgga gatttacaac aggctttggg agcagcgaat     540
aattggtcac cagatgatga tcacacactg ctaaaaaaga taaatccaaa cctttaccaa     600
ttatcgggga cacttccagc tggtacatac caatataaga tagccttgga ccattcttgg     660
aatacctcct atccaggtaa caatgtaagt cttactgttc ctcagggagg ggaaaaggtt     720
accttaacct atattccatc taccaaccag gtattcgata gcgtcaatca tcctaaccaa     780
gcattcccta catcctcagc aggggtccag acaaatttag tccaattgac tttagcgagt     840
gcaccggatg tcacccataa tttagatgta gcagcagacg gttacaaagc gcacaatatt     900
ttaccaagga atgttttaaa tctgccgcgg tatgattata gtggaaatga tttgggtaat     960
gtttattcaa aggatgcaac atccttccgg gtatgggctc aacagcttc gaatgtccag    1020 ttgcttttat acaatagtga gaaaggttca ataactaaac agcttgaaat gcaaaagagt    1080
```

```
gataacggta catggaaact tcaggtttct ggtaatcttg aaaactggta ttatctatat   1140
caagtcacag tgaatgggac aacacaaacg gcagttgatc catatgcgcg tgctatttct   1200
gtcaatgcaa cacgcggtat gattgtggac ctaaaagcta ccgatcctgc agggtggcag   1260
ggagatcatg aacagacacc tgcgaatcca gtagatgaag tgatttatga agcgcatgta   1320
cgcgattttt cgattgatgc taattcaggt atgaaaaata aagggaagta tttagcgttt   1380
acagagcatg gaacaaaagg accggatcat gtaaagacag gtattgatag tttgaaggaa   1440
ttgggcatca ccactgttca attgcaacct gttgaggagt ttaacagtat tgatgagacc   1500
cagcctgata cgtataactg gggctacgat ccaaggaact ataacgtacc agagggagct   1560
tatgccacaa ctccagaagg aacagcgcgt ataacagaat taaagcaatt aattcaaagc   1620
cttcatcagc agcggattgg tgtcaatatg gatgttgttt ataaccatac ctttgatgtg   1680
atggtttctg atttttgataa aattgtcccg caatattatt atcgtaccga tagtaatggc   1740
aattatacga acggatcagg ttgcggcaat gaattcgcga ctgagcatcc aatggcacaa   1800
aagtttgtgc ttgattcagt taattattgg gtaaatgagt accacgtgga tggcttccgt   1860
tttgacttaa tggctctttt aggaaaagac acgatggcaa aaatatcaaa cgagctgcat   1920
gccattaatc ctggtattgt tttatatgga gaaccatgga ctggcggcac atcgggatta   1980
tctagcgacc agcttgtaac gaagggtcaa caaaagggat taggaattgg cgttttcaac   2040
gataatatac gtaatgggct cgatgggaac gtgtttgata aaacggcaca aggctttgca   2100
acaggagatc caaaccaggt ggatgtcatt aaaaatggag taatcggtag tattcaagat   2160
tttacttcag cacctagcga aacgattaac tatgttacaa gccatgataa catgacgctt   2220
tgggataaaa ttttagcaag taatccaagt gacactgagg ctgaccgaat taaaatggat   2280
gaattggcac atgccgtagt attcacttca caaggtgtac catttatgca aggtggagaa   2340
gaaatgctga ggacaaaagg cggaaatgat aacagttata cgctggaga tagtgtgaat   2400 cagttcgact ggtcaagaaa ggcgcaattt aaggatgttt ttgactactt ttctagtatg   2460
attcatcttc gtaatcagca cccggcattc aggatgacga cagcggatca aattaaacag   2520
aatcttacat tcttagaaag cccaacaaac acggtagctt tcgagttaaa gaattatgca   2580
aaccatgata catggaaaaa tataattgtc atgtataacc caaataagac ttcccaaacc   2640
cttaatctac aagtggaga ttggaccatt gtaggattgg gagatcaaat aggtgagaaa   2700
tcattagggc atgtaatggg taatgttcaa gtaccggcta aagtacgct tattctcaaa   2760 caataa                                                             2766
```

<210> SEQ ID NO 2
<211> LENGTH: 921
<212> TYPE: PRT
<213> ORGANISM: Bacillus acidopullulyticus

<400> SEQUENCE: 2

```
Asp Ser Thr Ser Thr Lys Val Ile Val His Tyr His Arg Phe Asp Ser
1               5                   10                  15

Asn Tyr Thr Asn Trp Asp Val Trp Met Trp Pro Tyr Gln Pro Val Asn
            20                  25                  30

Gly Asn Gly Ala Ala Tyr Gln Phe Thr Gly Thr Asn Asp Asp Phe Gly
        35                  40                  45

Ala Val Ala Asp Thr Gln Val Pro Gly Asp Asn Thr Gln Val Gly Leu
    50                  55                  60
```

-continued

Ile Val Arg Lys Asn Asp Trp Ser Glu Lys Asn Thr Pro Asn Asp Leu
65                  70                  75                  80

His Ile Asp Leu Ala Lys Gly His Glu Val Trp Ile Val Gln Gly Asp
                85                  90                  95

Pro Thr Ile Tyr Tyr Asn Leu Ser Asp Ala Gln Ala Ala Ile Pro
            100                 105                 110

Ser Val Ser Asn Ala Tyr Leu Asp Asp Glu Lys Thr Val Leu Ala Lys
            115                 120                 125

Leu Ser Met Pro Met Thr Leu Ala Asp Ala Ala Ser Gly Phe Thr Val
            130                 135                 140

Ile Asp Lys Thr Thr Gly Glu Lys Ile Pro Val Thr Ser Ala Val Ser
145                 150                 155                 160

Ala Asn Pro Val Thr Ala Val Leu Val Gly Asp Leu Gln Gln Ala Leu
                165                 170                 175

Gly Ala Ala Asn Asn Trp Ser Pro Asp Asp His Thr Leu Leu Lys
            180                 185                 190

Lys Ile Asn Pro Asn Leu Tyr Gln Leu Ser Gly Thr Leu Pro Ala Gly
            195                 200                 205

Thr Tyr Gln Tyr Lys Ile Ala Leu Asp His Ser Trp Asn Thr Ser Tyr
            210                 215                 220

Pro Gly Asn Asn Val Ser Leu Thr Val Pro Gln Gly Gly Glu Lys Val
225                 230                 235                 240

Thr Phe Thr Tyr Ile Pro Ser Thr Asn Gln Val Phe Asp Ser Val Asn
                245                 250                 255

His Pro Asn Gln Ala Phe Pro Thr Ser Ser Ala Gly Val Gln Thr Asn
            260                 265                 270

Leu Val Gln Leu Thr Leu Ala Ser Ala Pro Asp Val Thr His Asn Leu
            275                 280                 285

Asp Val Ala Ala Asp Gly Tyr Lys Ala His Asn Ile Leu Pro Arg Asn
            290                 295                 300

Val Leu Asn Leu Pro Arg Tyr Asp Tyr Ser Gly Asn Asp Leu Gly Asn
305                 310                 315                 320

Val Tyr Ser Lys Asp Ala Thr Ser Phe Arg Val Trp Ala Pro Thr Ala
                325                 330                 335

Ser Asn Val Gln Leu Leu Leu Tyr Asn Ser Glu Lys Gly Ser Ile Thr
            340                 345                 350

Lys Gln Leu Glu Met Gln Lys Ser Asp Asn Gly Thr Trp Lys Leu Gln
            355                 360                 365

Val Ser Gly Asn Leu Glu Asn Trp Tyr Tyr Leu Tyr Gln Val Thr Val
            370                 375                 380

Asn Gly Thr Thr Gln Thr Ala Val Asp Pro Tyr Ala Arg Ala Ile Ser
385                 390                 395                 400

Val Asn Ala Thr Arg Gly Met Ile Val Asp Leu Lys Ala Thr Asp Pro
                405                 410                 415

Ala Gly Trp Gln Gly Asp His Glu Gln Thr Pro Ala Asn Pro Val Asp
            420                 425                 430

Glu Val Ile Tyr Glu Ala His Val Arg Asp Phe Ser Ile Asp Ala Asn
            435                 440                 445

Ser Gly Met Lys Asn Lys Gly Lys Tyr Leu Ala Phe Thr Glu His Gly
            450                 455                 460

Thr Lys Gly Pro Asp His Val Lys Thr Gly Ile Asp Ser Leu Lys Glu
465                 470                 475                 480

```
Leu Gly Ile Thr Thr Val Gln Leu Gln Pro Val Glu Phe Asn Ser
                485                 490                 495

Ile Asp Glu Thr Gln Pro Asp Thr Tyr Asn Trp Gly Tyr Asp Pro Arg
        500                 505                 510

Asn Tyr Asn Val Pro Glu Gly Ala Tyr Ala Thr Thr Pro Glu Gly Thr
            515                 520                 525

Ala Arg Ile Thr Glu Leu Lys Gln Leu Ile Gln Ser Leu His Gln Gln
        530                 535                 540

Arg Ile Gly Val Asn Met Asp Val Val Tyr Asn His Thr Phe Asp Val
545                 550                 555                 560

Met Val Ser Asp Phe Asp Lys Ile Val Pro Gln Tyr Tyr Arg Thr
                565                 570                 575

Asp Ser Asn Gly Asn Tyr Thr Asn Gly Ser Gly Cys Gly Asn Glu Phe
            580                 585                 590

Ala Thr Glu His Pro Met Ala Gln Lys Phe Val Leu Asp Ser Val Asn
        595                 600                 605

Tyr Trp Val Asn Glu Tyr His Val Asp Gly Phe Arg Phe Asp Leu Met
        610                 615                 620

Ala Leu Leu Gly Lys Asp Thr Met Ala Lys Ile Ser Asn Glu Leu His
625                 630                 635                 640

Ala Ile Asn Pro Gly Ile Val Leu Tyr Gly Glu Pro Trp Thr Gly Gly
            645                 650                 655

Thr Ser Gly Leu Ser Ser Asp Gln Leu Val Thr Lys Gly Gln Gln Lys
            660                 665                 670

Gly Leu Gly Ile Gly Val Phe Asn Asp Asn Ile Arg Asn Gly Leu Asp
        675                 680                 685

Gly Asn Val Phe Asp Lys Thr Ala Gln Gly Phe Ala Thr Gly Asp Pro
        690                 695                 700

Asn Gln Val Asp Val Ile Lys Asn Gly Val Ile Gly Ser Ile Gln Asp
705                 710                 715                 720

Phe Thr Ser Ala Pro Ser Glu Thr Ile Asn Tyr Val Thr Ser His Asp
            725                 730                 735

Asn Met Thr Leu Trp Asp Lys Ile Leu Ala Ser Asn Pro Ser Asp Thr
            740                 745                 750

Glu Ala Asp Arg Ile Lys Met Asp Glu Leu Ala His Ala Val Val Phe
        755                 760                 765

Thr Ser Gln Gly Val Pro Phe Met Gln Gly Gly Glu Glu Met Leu Arg
        770                 775                 780

Thr Lys Gly Gly Asn Asp Asn Ser Tyr Asn Ala Gly Asp Ser Val Asn
785                 790                 795                 800

Gln Phe Asp Trp Ser Arg Lys Ala Gln Phe Lys Asp Val Phe Asp Tyr
            805                 810                 815

Phe Ser Ser Met Ile His Leu Arg Asn Gln His Pro Ala Phe Arg Met
                820                 825                 830

Thr Thr Ala Asp Gln Ile Lys Gln Asn Leu Thr Phe Leu Glu Ser Pro
        835                 840                 845

Thr Asn Thr Val Ala Phe Glu Leu Lys Asn Tyr Ala Asn His Asp Thr
850                 855                 860

Trp Lys Asn Ile Ile Val Met Tyr Asn Pro Asn Lys Thr Ser Gln Thr
865                 870                 875                 880

Leu Asn Leu Pro Ser Gly Asp Trp Thr Ile Val Gly Leu Gly Asp Gln
                885                 890                 895
```

```
Ile Gly Glu Lys Ser Leu Gly His Val Met Gly Asn Val Gln Val Pro
            900                 905                 910

Ala Ile Ser Thr Leu Ile Leu Lys Gln
            915                 920

<210> SEQ ID NO 3
<211> LENGTH: 2787
<212> TYPE: DNA
<213> ORGANISM: Bacillus deramificans

<400> SEQUENCE: 3
gatgggaaca cgacaacgat cattgtccac tattttcgcc ctgctggtga ttatcaacct     60
tggagtctat ggatgtggcc aaaagacgga ggtggggctg aatacgattt caatcaaccg    120
gctgactctt ttggagctgt tgcaagtgct gatattccag gaaacccaag tcaggtagga    180
attatcgttc gcactcaaga ttggaccaaa gatgtgagcg ctgaccgcta catagattta    240
agcaaaggaa atgaggtgtg gcttgtagaa ggaaacagcc aaattttttta taatgaaaaa    300 gatgctgagg atgcagctaa acccgctgta agcaacgctt atttagatgc ttcaaaccag    360
gtgctggtta aacttagcca gccgttaact cttggggaag cgcaagcgg ctttacggtt    420 catgacgaca cagcaaataa ggatattcca gtgcatctg tgaaggatgc aagtcttggt    480
caagatgtaa ccgctgtttt ggcaggtacc ttccaacata tttttggagg ttccgattgg    540
gcacctgata atcacagtac tttattaaaa aaggtgacta caatctcta tcaattctca    600 ggagatcttc ctgaaggaaa ctaccaatat aaagtggctt taaatgatag ctggaataat    660
ccgagttacc catctgacaa cattaattta acagtccctg ccggcggtgc acacgtcact    720
ttttcgtata ttccgtccac tcatgcagtc tatgacacaa ttaataatcc taatgcggat    780
ttacaagtag aaagcggggt taaaacggat ctcgtgacgg ttactctagg gaagatccca    840
gatgtgagcc atactctgtc cattcaaaca gatggctatc aggcaaagca ggtgatacct    900
cgtaatgtgc ttaattcatc acagtactac tattcaggag atgatcttgg gaataccatt    960
acacagaaag caacaacctt taaagtctgg gcaccaactt ctactcaagt aaatgttctt   1020
ctttatgaca gtgcaacggg ttctgtaaca aaaatcgtac ctatgacggc atcgggccat   1080
ggtgtgtggg aagcaacggt taatcaaaac cttgaaaatt ggtattacat gtatgaggta   1140
acaggccaag gctctacccg aacggctgtt gatccttatg caactgcgat tgcaccaaat   1200
ggaacgagag gcatgattgt ggacctggct aaaacagatc ctgctggctg aacagtgat    1260 aaacatatta cgccaaagaa tatagaagat gaggtcatct atgaaatgga tgtccgtgac   1320
ttttccattg accctaattc gggtatgaaa aataaaggga agtatttggc tcttacagaa   1380
aaaggaacaa agggccctga caacgtaaag acggggatag attccttaaa caacttgggg   1440
attactcatg ttcagcttat gcctgttttc gcatctaaca gtgtcgatga aactgatcca   1500
acccaagata attggggtta tgaccctcgc aactatgatg ttcctgaagg cagtatgct    1560 acaaatgcga atggtaatgc tcgtataaaa gagtttaagg aaatggttct ttcactccat   1620
cgtgaacaca ttggggttaa catggatgtt gtctataatc ataccttgc cacgcaaatc    1680 tctgacttcg ataaaattgt accagaatat tattaccgta cggatgatgc aggtaattat   1740
accaacggat caggtactgg aaatgaaatt gcagccgaaa ggccaatggt tcaaaaattt    1800
attattgatt cccttaagta tgggtcaat gagtatcata ttgacggctt ccgttttgac   1860
ttaatggcgc tgcttggaaa agacacgatg tccaaagctg cctcggagct tcatgctatt   1920
aatccaggaa ttgcacttta cggtgagcca tggacgggtg aacctctgc actgccagat   1980
```

-continued

```
gatcagcttc tgacaaaagg agctcaaaaa ggcatgggag tagcggtgtt taatgacaat      2040
ttacgaaacg cgttggacgg caatgtcttt gattcttccg ctcaaggttt tgcgacaggt      2100
gcaacaggct taactgatgc aattaagaat ggcgttgagg ggagtattaa tgactttacc      2160
tcttcaccag gtgagacaat taactatgtc acaagtcatg ataactacac cctttgggac      2220
aaaatagccc taagcaatcc taatgattcc gaagcggatc ggattaaaat ggatgaactc      2280
gcacaagcag ttgttatgac ctcacaaggc gttccattca tgcaaggcgg ggaagaaatg      2340
cttcgtacaa aaggcggcaa cgacaatagt tataatgcag gcgatgcggt caatgagttt      2400
gattggagca ggaaagctca atatccagat gttttcaact attatagcgg gctaatccac      2460
cttcgtcttg atcacccagc cttccgcatg acgacagcta atgaaatcaa tagccacctc      2520
caattcctaa atagtccaga gaacacagtg gcctatgaat taactgatca tgttaataaa      2580
gacaaatggg gaaatatcat tgttgtttat aacccaaata aaactgtagc aaccatcaat      2640
ttgccgagcg ggaaatgggc aatcaatgct acgagcggta aggtaggaga atccacccct      2700
ggtcaagcag agggaagtgt ccaagtacca ggtatatcta tgatgatcct tcatcaagag      2760
gtaagcccag accacggtaa aaagtaa                                          2787
```

<210> SEQ ID NO 4
<211> LENGTH: 928
<212> TYPE: PRT
<213> ORGANISM: Bacillus deramificans

<400> SEQUENCE: 4

```
Asp Gly Asn Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly
                20                  25                  30

Ala Glu Tyr Asp Phe Asn Gln Pro Ala Asp Ser Phe Gly Ala Val Ala
            35                  40                  45

Ser Ala Asp Ile Pro Gly Asn Pro Ser Gln Val Gly Ile Ile Val Arg
        50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
                85                  90                  95

Tyr Asn Glu Lys Asp Ala Glu Asp Ala Ala Lys Pro Ala Val Ser Asn
                100                 105                 110

Ala Tyr Leu Asp Ala Ser Asn Gln Val Leu Val Lys Leu Ser Gln Pro
            115                 120                 125

Leu Thr Leu Gly Glu Gly Ala Ser Gly Phe Thr Val His Asp Asp Thr
        130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
                165                 170                 175

Gly Ser Asp Trp Ala Pro Asp Asn His Ser Thr Leu Leu Lys Lys Val
                180                 185                 190

Thr Asn Asn Leu Tyr Gln Phe Ser Gly Asp Leu Pro Glu Gly Asn Tyr
            195                 200                 205

Gln Tyr Lys Val Ala Leu Asn Asp Ser Trp Asn Asn Pro Ser Tyr Pro
        210                 215                 220
```

-continued

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
            245                 250                 255

Pro Asn Ala Asp Leu Gln Val Glu Ser Gly Val Lys Thr Asp Leu Val
        260                 265                 270

Thr Val Thr Leu Gly Glu Asp Pro Asp Val Ser His Thr Leu Ser Ile
    275                 280                 285

Gln Thr Asp Gly Tyr Gln Ala Lys Gln Val Ile Pro Arg Asn Val Leu
290                 295                 300

Asn Ser Ser Gln Tyr Tyr Tyr Ser Gly Asp Asp Leu Gly Asn Thr Tyr
305                 310                 315                 320

Thr Gln Lys Ala Thr Thr Phe Lys Val Trp Ala Pro Thr Ser Thr Gln
                325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
        355                 360                 365

Gln Asn Leu Glu Asn Trp Tyr Tyr Met Tyr Glu Val Thr Gly Gln Gly
370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
        435                 440                 445

Met Lys Asn Lys Gly Lys Tyr Leu Ala Leu Thr Glu Lys Gly Thr Lys
450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
        515                 520                 525

Ile Lys Glu Phe Lys Glu Met Val Leu Ser Leu His Arg Glu His Ile
530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
610                 615                 620

Leu Gly Lys Asp Thr Met Ser Lys Ala Ala Ser Glu Leu His Ala Ile
625                 630                 635                 640

```
Asn Pro Gly Ile Ala Leu Tyr Gly Glu Pro Trp Thr Gly Gly Thr Ser
            645                 650                 655

Ala Leu Pro Asp Asp Gln Leu Leu Thr Lys Gly Ala Gln Lys Gly Met
        660                 665                 670

Gly Val Ala Val Phe Asn Asp Asn Leu Arg Asn Ala Leu Asp Gly Asn
    675                 680                 685

Val Phe Asp Ser Ser Ala Gln Gly Phe Ala Thr Gly Ala Thr Gly Leu
690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
                725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
        755                 760                 765

Gln Gly Val Pro Phe Met Gln Gly Gly Glu Glu Met Leu Arg Thr Lys
    770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
        835                 840                 845

Thr Val Ala Tyr Glu Leu Thr Asp His Val Asn Lys Asp Lys Trp Gly
    850                 855                 860

Asn Ile Ile Val Val Tyr Asn Pro Asn Lys Thr Val Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
        915                 920                 925

<210> SEQ ID NO 5
<211> LENGTH: 2505
<212> TYPE: DNA
<213> ORGANISM: Bacillus deramificans

<400> SEQUENCE: 5
attttttata atgaaaaaga tgctgaggat gcagctaaac ccgctgtaag caacgcttat      60
ttagatgctt caaaccaggt gctggttaaa cttagccagc cgttaactct tggggaaggc     120
gcaagcggct ttacggttca tgacgacaca gcaaataagg atattccagt gacatctgtg     180
aaggatgcaa gtcttggtca gatgtaacc gctgttttgg caggtacctt ccaacatatt      240
tttggaggtt ccgattgggc acctgataat cacagtactt attaaaaaa ggtgactaac      300 aatctctatc aattctcagg agatcttcct gaaggaaact accaatataa agtggcttta     360
aatgatagct ggaataatcc gagttaccca tctgacaaca ttaatttaac agtccctgcc     420
ggcggtgcac acgtcacttt ttcgtatatt ccgtccactc atgcagtcta tgacacaatt     480
aataatccta tgcggattt acaagtagaa agcggggtta aaacggatct cgtgacggtt     540
```

```
actctagggg aagatccaga tgtgagccat actctgtcca ttcaaacaga tggctatcag    600
gcaaagcagg tgatacctcg taatgtgctt aattcatcac agtactacta ttcaggagat    660
gatcttggga atacctatac acagaaagca acaaccttta aagtctgggc accaacttct    720
actcaagtaa atgttcttct ttatgacagt gcaacgggtt ctgtaacaaa atcgtacct    780 atgacggcat cgggccatgg tgtgtgggaa gcaacggtta atcaaaacct tgaaaattgg    840
tattacatgt atgaggtaac aggccaaggc tctacccgaa cggctgttga tccttatgca    900
actgcgattg caccaaatgg aacgagaggc atgattgtgg acctggctaa acagatcct    960 gctggctgga acagtgataa acatattacg ccaaagaata tagaagatga ggtcatctat   1020
gaaatggatg tccgtgactt ttccattgac cctaattcgg gtatgaaaaa taagggaag   1080 tatttggctc ttacagaaaa aggaacaaag ggccctgaca acgtaaagac ggggatagat   1140
tccttaaaac aacttgggat tactcatgtt cagcttatgc ctgttttcgc atctaacagt   1200
gtcgatgaaa ctgatccaac ccaagataat tggggttatg accctcgcaa ctatgatgtt   1260
cctgaagggc agtatgctac aaatgcgaat ggtaatgctc gtataaaaga gtttaaggaa   1320
atggttcttt cactccatcg tgaacacatt ggggttaaca tggatgttgt ctataatcat   1380
acctttgcca cgcaaatctc tgacttcgat aaaattgtac cagaatatta ttaccgtacg   1440
gatgatgcag gtaattatac caacggatca ggtactggaa atgaaattgc agccgaaagg   1500
ccaatggttc aaaaatttat tattgattcc cttaagtatt gggtcaatga gtatcatatt   1560
gacggcttcc gttttgactt aatggcgctg cttggaaaag acacgatgtc caaagctgcc   1620
tcggagcttc atgctattaa tccaggaatt gcacttacg gtgagccatg gacgggtgga   1680
acctctgcac tgccagatga tcagcttctg acaaaaggag ctcaaaaagg catgggagta   1740
gcggtgttta atgacaattt acgaaacgcg ttggacggca atgtctttga ttcttccgct   1800
caaggttttg cgacaggtgc aacaggctta actgatgcaa ttaagaatgg cgttgagggg   1860
agtattaatg actttacctc ttcaccaggt gagacaatta actatgtcac aagtcatgat   1920
aactacaccc tttgggacaa aatagcccta agcaatccta atgattccga agcggatcgg   1980
attaaaatgg atgaactcgc acaagcagtt gttatgacct cacaaggcgt tccattcatg   2040
caaggcgggg aagaaatgct tcgtacaaaa ggcggcaacg acaatagtta taatgcaggc   2100
gatgcggtca atgagtttga ttggagcagg aaagctcaat atccagatgt tttcaactat   2160
tatagcgggc taatccacct tcgtcttgat cacccagcct tccgcatgac gacagctaat   2220
gaaatcaata gccacctcca attcctaaat agtccagaga acacagtggc ctatgaatta   2280
actgatcatg ttaataaaga caaatgggga aatatcattg ttgtttataa cccaaataaa   2340
actgtagcaa ccatcaattt gccgagcggg aaatgggcaa tcaatgctac gagcggtaag   2400
gtaggagaat ccacccttgg tcaagcagag ggaagtgtcc aagtaccagg tatatctatg   2460
atgatccttc atcaagaggt aagcccagac cacggtaaaa agtaa                  2505
```

<210> SEQ ID NO 6
<211> LENGTH: 834
<212> TYPE: PRT
<213> ORGANISM: Bacillus deramificans

<400> SEQUENCE: 6

Ile Phe Tyr Asn Glu Lys Asp Ala Glu Asp Ala Ala Lys Pro Ala Val
1               5                   10                  15

Ser Asn Ala Tyr Leu Asp Ala Ser Asn Gln Val Leu Val Lys Leu Ser
            20                  25                  30

```
Gln Pro Leu Thr Leu Gly Glu Gly Ala Ser Gly Phe Thr Val His Asp
         35                  40                  45

Asp Thr Ala Asn Lys Asp Ile Pro Val Thr Ser Val Lys Asp Ala Ser
 50                  55                  60

Leu Gly Gln Asp Val Thr Ala Val Leu Ala Gly Thr Phe Gln His Ile
 65                  70                  75                  80

Phe Gly Gly Ser Asp Trp Ala Pro Asp Asn His Ser Thr Leu Leu Lys
                 85                  90                  95

Lys Val Thr Asn Asn Leu Tyr Gln Phe Ser Gly Asp Leu Pro Glu Gly
                100                 105                 110

Asn Tyr Gln Tyr Lys Val Ala Leu Asn Asp Ser Trp Asn Asn Pro Ser
            115                 120                 125

Tyr Pro Ser Asp Asn Ile Asn Leu Thr Val Pro Ala Gly Gly Ala His
        130                 135                 140

Val Thr Phe Ser Tyr Ile Pro Ser Thr His Ala Val Tyr Asp Thr Ile
145                 150                 155                 160

Asn Asn Pro Asn Ala Asp Leu Gln Val Glu Ser Gly Val Lys Thr Asp
                165                 170                 175

Leu Val Thr Val Thr Leu Gly Glu Asp Pro Asp Val Ser His Thr Leu
            180                 185                 190

Ser Ile Gln Thr Asp Gly Tyr Gln Ala Lys Gln Val Ile Pro Arg Asn
        195                 200                 205

Val Leu Asn Ser Ser Gln Tyr Tyr Tyr Ser Gly Asp Asp Leu Gly Asn
    210                 215                 220

Thr Tyr Thr Gln Lys Ala Thr Thr Phe Lys Val Trp Ala Pro Thr Ser
225                 230                 235                 240

Thr Gln Val Asn Val Leu Leu Tyr Asp Ser Ala Thr Gly Ser Val Thr
                245                 250                 255

Lys Ile Val Pro Met Thr Ala Ser Gly His Gly Val Trp Glu Ala Thr
            260                 265                 270

Val Asn Gln Asn Leu Glu Asn Trp Tyr Tyr Met Tyr Glu Val Thr Gly
        275                 280                 285

Gln Gly Ser Thr Arg Thr Ala Val Asp Pro Tyr Ala Thr Ala Ile Ala
    290                 295                 300

Pro Asn Gly Thr Arg Gly Met Ile Val Asp Leu Ala Lys Thr Asp Pro
305                 310                 315                 320

Ala Gly Trp Asn Ser Asp Lys His Ile Thr Pro Lys Asn Ile Glu Asp
                325                 330                 335

Glu Val Ile Tyr Glu Met Asp Val Arg Asp Phe Ser Ile Asp Pro Asn
            340                 345                 350

Ser Gly Met Lys Asn Lys Gly Lys Tyr Leu Ala Leu Thr Glu Lys Gly
        355                 360                 365

Thr Lys Gly Pro Asp Asn Val Lys Thr Gly Ile Asp Ser Leu Lys Gln
    370                 375                 380

Leu Gly Ile Thr His Val Gln Leu Met Pro Val Phe Ala Ser Asn Ser
385                 390                 395                 400

Val Asp Glu Thr Asp Pro Thr Gln Asp Asn Trp Gly Tyr Asp Pro Arg
                405                 410                 415

Asn Tyr Asp Val Pro Glu Gly Gln Tyr Ala Thr Asn Ala Asn Gly Asn
            420                 425                 430

Ala Arg Ile Lys Glu Phe Lys Glu Met Val Leu Ser Leu His Arg Glu
        435                 440                 445
```

His Ile Gly Val Asn Met Asp Val Val Tyr Asn His Thr Phe Ala Thr
450                 455                 460

Gln Ile Ser Asp Phe Asp Lys Ile Val Pro Glu Tyr Tyr Arg Thr
465                 470                 475                 480

Asp Asp Ala Gly Asn Tyr Thr Asn Gly Ser Gly Thr Gly Asn Glu Ile
            485                 490                 495

Ala Ala Glu Arg Pro Met Val Gln Lys Phe Ile Ile Asp Ser Leu Lys
        500                 505                 510

Tyr Trp Val Asn Glu Tyr His Ile Asp Gly Phe Arg Phe Asp Leu Met
    515                 520                 525

Ala Leu Leu Gly Lys Asp Thr Met Ser Lys Ala Ala Ser Glu Leu His
530                 535                 540

Ala Ile Asn Pro Gly Ile Ala Leu Tyr Gly Glu Pro Trp Thr Gly Gly
545                 550                 555                 560

Thr Ser Ala Leu Pro Asp Asp Gln Leu Leu Thr Lys Gly Ala Gln Lys
            565                 570                 575

Gly Met Gly Val Ala Val Phe Asn Asp Asn Leu Arg Asn Ala Leu Asp
        580                 585                 590

Gly Asn Val Phe Asp Ser Ser Ala Gln Gly Phe Ala Thr Gly Ala Thr
    595                 600                 605

Gly Leu Thr Asp Ala Ile Lys Asn Gly Val Glu Gly Ser Ile Asn Asp
610                 615                 620

Phe Thr Ser Ser Pro Gly Glu Thr Ile Asn Tyr Val Thr Ser His Asp
625                 630                 635                 640

Asn Tyr Thr Leu Trp Asp Lys Ile Ala Leu Ser Asn Pro Asn Asp Ser
            645                 650                 655

Glu Ala Asp Arg Ile Lys Met Asp Glu Leu Ala Gln Ala Val Val Met
        660                 665                 670

Thr Ser Gln Gly Val Pro Phe Met Gln Gly Gly Glu Glu Met Leu Arg
    675                 680                 685

Thr Lys Gly Gly Asn Asp Asn Ser Tyr Asn Ala Gly Asp Ala Val Asn
690                 695                 700

Glu Phe Asp Trp Ser Arg Lys Ala Gln Tyr Pro Asp Val Phe Asn Tyr
705                 710                 715                 720

Tyr Ser Gly Leu Ile His Leu Arg Leu Asp His Pro Ala Phe Arg Met
            725                 730                 735

Thr Thr Ala Asn Glu Ile Asn Ser His Leu Gln Phe Leu Asn Ser Pro
        740                 745                 750

Glu Asn Thr Val Ala Tyr Glu Leu Thr Asp His Val Asn Lys Asp Lys
    755                 760                 765

Trp Gly Asn Ile Ile Val Val Tyr Asn Pro Asn Lys Thr Val Ala Thr
770                 775                 780

Ile Asn Leu Pro Ser Gly Lys Trp Ala Ile Asn Ala Thr Ser Gly Lys
785                 790                 795                 800

Val Gly Glu Ser Thr Leu Gly Gln Ala Glu Gly Ser Val Gln Val Pro
            805                 810                 815

Gly Ile Ser Met Met Ile Leu His Gln Glu Val Ser Pro Asp His Gly
        820                 825                 830

Lys Lys

<210> SEQ ID NO 7
<211> LENGTH: 2475
<212> TYPE: DNA
<213> ORGANISM: Bacillus deramificans

<400> SEQUENCE: 7

```
gcagctaaac cgctgtaagc caacgcttat ttagatgctt caaaccaggt gctggttaaa      60
cttagccagc cgttaactct tggggaaggc gcaagcggct ttacggttca tgacgacaca     120
gcaaataagg atattccagt gacatctgtg aaggatgcaa gtcttggtca agatgtaacc     180
gctgttttgg caggtacctt ccaacatatt tttggaggtt ccgattgggc acctgataat     240
cacagtactt tattaaaaaa ggtgactaac aatctctatc aattctcagg agatcttcct     300
gaaggaaact accaatataa agtggcttta atgatagct ggaataatcc gagttaccca     360
tctgacaaca ttaatttaac agtccctgcc ggcggtgcac acgtcacttt ttcgtatatt     420
ccgtccactc atgcagtcta tgacacaatt aataatccta atgcggattt acaagtagaa     480
agcggggtta aaacggatct cgtgacggtt actctagggg aagatccaga tgtgagccat     540
actctgtcca ttcaaacaga tggctatcag gcaaagcagg tgatacctcg taatgtgctt     600
aattcatcac agtactacta ttcaggagat gatcttggga atacctatac acagaaagca     660
acaacctta aagtctgggc accaacttct actcaagtaa atgttcttct ttatgacagt     720
gcaacgggtt ctgtaacaaa aatcgtacct atgacggcat cgggccatgg tgtgtgggaa     780
gcaacggtta atcaaaacct tgaaaattgg tattacatgt atgaggtaac aggccaaggc     840
tctacccgaa cggctgttga tccttatgca actgcgattg caccaaatgg aacgagaggc     900
atgattgtgg acctggctaa aacagatcct gctggctgga cagtgataaa catattacg     960
ccaaagaata tagaagatga ggtcatctat gaaatggatg tccgtgactt ttccattgac    1020
cctaattcgg gtatgaaaaa taaagggaag tatttggctc ttacagaaaa aggaacaaag    1080
ggccctgaca acgtaaagac ggggatagat tccttaaaac aacttgggat tactcatgtt    1140
cagcttatgc ctgttttcgc atctaacagt gtcgatgaaa ctgatccaac ccaagataat    1200
tggggttatg accctcgcaa ctatgatgtt cctgaagggc agtatgctac aaatgcgaat    1260
ggtaatgctc gtataaaaga gtttaaggaa atggttcttt cactccatcg tgaacacatt    1320
ggggttaaca tggatgttgt ctataatcat acctttgcca cgcaaatctc tgacttcgat    1380
aaaattgtac cagaatatta ttaccgtacg gatgatgcag gtaattatac caacggatca    1440
ggtactggaa atgaaattgc agccgaaagg ccaatggttc aaaaatttat tattgattcc    1500
cttaagtatt gggtcaatga gtatcatatt gacggcttcc gttttgactt aatgcgcctg    1560
cttggaaaag acacgatgtc caaagctgcc tcggagcttc atgctattaa tccaggaatt    1620
gcactttacg gtgagccatg gacgggtgga acctctgcac tgccagatga tcagcttctg    1680
acaaaaggag ctcaaaaagg catgggagta gcggtgttta tgacaatttt acgaaacgcg    1740
ttggacggca atgtctttga ttcttccgct caaggttttg cgacaggtgc aacaggctta    1800
actgatgcaa ttaagaatgg cgttgagggg agtattaatg actttacctc ttcaccaggt    1860
gagacaatta actatgtcac aagtcatgat aactacaccc tttgggacaa aatagcccta    1920
agcaatccta atgattccga agcggatcgg attaaaatgg atgaactcgc acaagcagtt    1980
gttatgacct cacaaggcgt tccattcatg caaggcgggg aagaaatgct tcgtacaaaa    2040
ggcggcaacg acaatagtta taatgcaggc gatgcggtca atgagtttga ttggagcagg    2100
aaagctcaat atccagatgt tttcaactat tatagcgggc taatccacct tcgtcttgat    2160
cacccagcct tccgcatgac gacagctaat gaaatcaata gccacctcca attcctaaat    2220
agtccagaga cacagtggc ctatgaatta actgatcatg ttaataaaga caatggggga    2280
aatatcattg ttgtttataa cccaaataaa actgtagcaa ccatcaattt gccgagcggg    2340
```

```
aaatgggcaa tcaatgctac gagcggtaag gtaggagaat ccaccccttgg tcaagcagag    2400 ggaagtgtcc aagtaccagg tatatctatg atgatccttc atcaagaggt aagcccagac    2460
cacggtaaaa agtaa                                                      2475
```

<210> SEQ ID NO 8
<211> LENGTH: 824
<212> TYPE: PRT
<213> ORGANISM: Bacillus deramificans

<400> SEQUENCE: 8

```
Ala Ala Lys Pro Ala Val Ser Asn Ala Tyr Leu Asp Ala Ser Asn Gln
1               5                   10                  15

Val Leu Val Lys Leu Ser Gln Pro Leu Thr Leu Gly Glu Gly Ala Ser
                20                  25                  30

Gly Phe Thr Val His Asp Asp Thr Ala Asn Lys Asp Ile Pro Val Thr
            35                  40                  45

Ser Val Lys Asp Ala Ser Leu Gly Gln Asp Val Thr Ala Val Leu Ala
50                  55                  60

Gly Thr Phe Gln His Ile Phe Gly Gly Ser Asp Trp Ala Pro Asp Asn
65                  70                  75                  80

His Ser Thr Leu Leu Lys Lys Val Thr Asn Asn Leu Tyr Gln Phe Ser
                85                  90                  95

Gly Asp Leu Pro Glu Gly Asn Tyr Gln Tyr Lys Val Ala Leu Asn Asp
            100                 105                 110

Ser Trp Asn Asn Pro Ser Tyr Pro Ser Asp Asn Ile Asn Leu Thr Val
        115                 120                 125

Pro Ala Gly Gly Ala His Val Thr Phe Ser Tyr Ile Pro Ser Thr His
130                 135                 140

Ala Val Tyr Asp Thr Ile Asn Asn Pro Asn Ala Asp Leu Gln Val Glu
145                 150                 155                 160

Ser Gly Val Lys Thr Asp Leu Val Thr Val Thr Leu Gly Glu Asp Pro
                165                 170                 175

Asp Val Ser His Thr Leu Ser Ile Gln Thr Asp Gly Tyr Gln Ala Lys
            180                 185                 190

Gln Val Ile Pro Arg Asn Val Leu Asn Ser Ser Gln Tyr Tyr Tyr Ser
        195                 200                 205

Gly Asp Asp Leu Gly Asn Thr Tyr Thr Gln Lys Ala Thr Thr Phe Lys
210                 215                 220

Val Trp Ala Pro Thr Ser Thr Gln Val Asn Val Leu Leu Tyr Asp Ser
225                 230                 235                 240

Ala Thr Gly Ser Val Thr Lys Ile Val Pro Met Thr Ala Ser Gly His
                245                 250                 255

Gly Val Trp Glu Ala Thr Val Asn Gln Asn Leu Glu Asn Trp Tyr Tyr
            260                 265                 270

Met Tyr Glu Val Thr Gly Gln Gly Ser Thr Arg Thr Ala Val Asp Pro
        275                 280                 285

Tyr Ala Thr Ala Ile Ala Pro Asn Gly Thr Arg Gly Met Ile Val Asp
290                 295                 300

Leu Ala Lys Thr Asp Pro Ala Gly Trp Asn Ser Asp Lys His Ile Thr
305                 310                 315                 320

Pro Lys Asn Ile Glu Asp Glu Val Ile Tyr Glu Met Asp Val Arg Asp
                325                 330                 335

Phe Ser Ile Asp Pro Asn Ser Gly Met Lys Asn Lys Gly Lys Tyr Leu
            340                 345                 350
```

```
Ala Leu Thr Glu Lys Gly Thr Lys Gly Pro Asp Asn Val Lys Thr Gly
            355                 360                 365

Ile Asp Ser Leu Lys Gln Leu Gly Ile Thr His Val Gln Leu Met Pro
        370                 375                 380

Val Phe Ala Ser Asn Ser Val Asp Glu Thr Asp Pro Thr Gln Asp Asn
385                 390                 395                 400

Trp Gly Tyr Asp Pro Arg Asn Tyr Asp Val Pro Glu Gly Gln Tyr Ala
                405                 410                 415

Thr Asn Ala Asn Gly Asn Ala Arg Ile Lys Glu Phe Lys Glu Met Val
                420                 425                 430

Leu Ser Leu His Arg Glu His Ile Gly Val Asn Met Asp Val Val Tyr
            435                 440                 445

Asn His Thr Phe Ala Thr Gln Ile Ser Asp Phe Asp Lys Ile Val Pro
        450                 455                 460

Glu Tyr Tyr Tyr Arg Thr Asp Asp Ala Gly Asn Tyr Thr Asn Gly Ser
465                 470                 475                 480

Gly Thr Gly Asn Glu Ile Ala Ala Glu Arg Pro Met Val Gln Lys Phe
                485                 490                 495

Ile Ile Asp Ser Leu Lys Tyr Trp Val Asn Glu Tyr His Ile Asp Gly
                500                 505                 510

Phe Arg Phe Asp Leu Met Ala Leu Leu Gly Lys Asp Thr Met Ser Lys
            515                 520                 525

Ala Ala Ser Glu Leu His Ala Ile Asn Pro Gly Ile Ala Leu Tyr Gly
        530                 535                 540

Glu Pro Trp Thr Gly Gly Thr Ser Ala Leu Pro Asp Asp Gln Leu Leu
545                 550                 555                 560

Thr Lys Gly Ala Gln Lys Gly Met Gly Val Ala Val Phe Asn Asp Asn
                565                 570                 575

Leu Arg Asn Ala Leu Asp Gly Asn Val Phe Asp Ser Ser Ala Gln Gly
                580                 585                 590

Phe Ala Thr Gly Ala Thr Gly Leu Thr Asp Ala Ile Lys Asn Gly Val
            595                 600                 605

Glu Gly Ser Ile Asn Asp Phe Thr Ser Ser Pro Gly Glu Thr Ile Asn
        610                 615                 620

Tyr Val Thr Ser His Asp Asn Tyr Thr Leu Trp Asp Lys Ile Ala Leu
625                 630                 635                 640

Ser Asn Pro Asn Asp Ser Glu Ala Asp Arg Ile Lys Met Asp Glu Leu
                645                 650                 655

Ala Gln Ala Val Val Met Thr Ser Gln Gly Val Pro Phe Met Gln Gly
                660                 665                 670

Gly Glu Glu Met Leu Arg Thr Lys Gly Gly Asn Asp Asn Ser Tyr Asn
            675                 680                 685

Ala Gly Asp Ala Val Asn Glu Phe Asp Trp Ser Arg Lys Ala Gln Tyr
        690                 695                 700

Pro Asp Val Phe Asn Tyr Tyr Ser Gly Leu Ile His Leu Arg Leu Asp
705                 710                 715                 720

His Pro Ala Phe Arg Met Thr Thr Ala Asn Glu Ile Asn Ser His Leu
                725                 730                 735

Gln Phe Leu Asn Ser Pro Glu Asn Thr Val Ala Tyr Glu Leu Thr Asp
                740                 745                 750

His Val Asn Lys Asp Lys Trp Gly Asn Ile Ile Val Val Tyr Asn Pro
            755                 760                 765
```

-continued

```
Asn Lys Thr Val Ala Thr Ile Asn Leu Pro Ser Gly Lys Trp Ala Ile
770                 775                 780

Asn Ala Thr Ser Gly Lys Val Gly Glu Ser Thr Leu Gly Gln Ala Glu
785                 790                 795                 800

Gly Ser Val Gln Val Pro Gly Ile Ser Met Met Ile Leu His Gln Glu
                805                 810                 815

Val Ser Pro Asp His Gly Lys Lys
                820

<210> SEQ ID NO 9
<211> LENGTH: 826
<212> TYPE: PRT
<213> ORGANISM: Bacillus deramificans

<400> SEQUENCE: 9

Glu Asp Ala Ala Lys Pro Ala Val Ser Asn Ala Tyr Leu Asp Ala Ser
1               5                   10                  15

Asn Gln Val Leu Val Lys Leu Ser Gln Pro Leu Thr Leu Gly Glu Gly
                20                  25                  30

Ala Ser Gly Phe Thr Val His Asp Asp Thr Ala Asn Lys Asp Ile Pro
            35                  40                  45

Val Thr Ser Val Lys Asp Ala Ser Leu Gly Gln Asp Val Thr Ala Val
        50                  55                  60

Leu Ala Gly Thr Phe Gln His Ile Phe Gly Gly Ser Asp Trp Ala Pro
65                  70                  75                  80

Asp Asn His Ser Thr Leu Leu Lys Lys Val Thr Asn Asn Leu Tyr Gln
                85                  90                  95

Phe Ser Gly Asp Leu Pro Glu Gly Asn Tyr Gln Tyr Lys Val Ala Leu
                100                 105                 110

Asn Asp Ser Trp Asn Asn Pro Ser Tyr Pro Ser Asp Asn Ile Asn Leu
            115                 120                 125

Thr Val Pro Ala Gly Gly Ala His Val Thr Phe Ser Tyr Ile Pro Ser
        130                 135                 140

Thr His Ala Val Tyr Asp Thr Ile Asn Asn Pro Asn Ala Asp Leu Gln
145                 150                 155                 160

Val Glu Ser Gly Val Lys Thr Asp Leu Val Thr Val Thr Leu Gly Glu
                165                 170                 175

Asp Pro Asp Val Ser His Thr Leu Ser Ile Gln Thr Asp Gly Tyr Gln
                180                 185                 190

Ala Lys Gln Val Ile Pro Arg Asn Val Leu Asn Ser Ser Gln Tyr Tyr
            195                 200                 205

Tyr Ser Gly Asp Asp Leu Gly Asn Thr Tyr Thr Gln Lys Ala Thr Thr
        210                 215                 220

Phe Lys Val Trp Ala Pro Thr Ser Thr Gln Val Asn Val Leu Leu Tyr
225                 230                 235                 240

Asp Ser Ala Thr Gly Ser Val Thr Lys Ile Val Pro Met Thr Ala Ser
                245                 250                 255

Gly His Gly Val Trp Glu Ala Thr Val Asn Gln Asn Leu Glu Asn Trp
                260                 265                 270

Tyr Tyr Met Tyr Glu Val Thr Gly Gln Gly Ser Thr Arg Thr Ala Val
            275                 280                 285

Asp Pro Tyr Ala Thr Ala Ile Ala Pro Asn Gly Thr Arg Gly Met Ile
        290                 295                 300

Val Asp Leu Ala Lys Thr Asp Pro Ala Gly Trp Asn Ser Asp Lys His
305                 310                 315                 320
```

```
Ile Thr Pro Lys Asn Ile Glu Asp Glu Val Ile Tyr Glu Met Asp Val
            325                 330                 335

Arg Asp Phe Ser Ile Asp Pro Asn Ser Gly Met Lys Asn Lys Gly Lys
            340                 345                 350

Tyr Leu Ala Leu Thr Glu Lys Gly Thr Lys Gly Pro Asp Asn Val Lys
            355                 360                 365

Thr Gly Ile Asp Ser Leu Lys Gln Leu Gly Ile Thr His Val Gln Leu
    370                 375                 380

Met Pro Val Phe Ala Ser Asn Ser Val Asp Glu Thr Asp Pro Thr Gln
385                 390                 395                 400

Asp Asn Trp Gly Tyr Asp Pro Arg Asn Tyr Asp Val Pro Gly Gly Gln
                405                 410                 415

Tyr Ala Thr Asn Ala Asn Gly Asn Ala Arg Ile Lys Glu Phe Lys Glu
            420                 425                 430

Met Val Leu Ser Leu His Arg Glu His Ile Gly Val Asn Met Asp Val
            435                 440                 445

Val Tyr Asn His Thr Phe Ala Thr Gln Ile Ser Asp Phe Asp Lys Ile
    450                 455                 460

Val Pro Glu Tyr Tyr Arg Thr Asp Ala Gly Asn Tyr Thr Asn
465                 470                 475             480

Gly Ser Gly Thr Gly Asn Glu Ile Ala Ala Glu Arg Pro Met Val Gln
                485                 490                 495

Lys Phe Ile Ile Asp Ser Leu Lys Tyr Trp Val Asn Glu Tyr His Ile
                500                 505                 510

Asp Gly Phe Arg Phe Asp Leu Met Ala Leu Leu Gly Lys Asp Thr Met
            515                 520                 525

Ser Lys Ala Ala Ser Glu Leu His Ala Ile Asn Pro Gly Ile Ala Leu
            530                 535                 540

Tyr Gly Glu Pro Trp Thr Gly Gly Thr Ser Ala Leu Pro Asp Asp Gln
545                 550                 555                 560

Leu Leu Thr Lys Gly Ala Gln Lys Gly Met Gly Val Ala Val Phe Asn
                565                 570                 575

Asp Asn Leu Arg Asn Ala Leu Asp Gly Asn Val Phe Asp Ser Ser Ala
            580                 585                 590

Gln Gly Phe Ala Thr Gly Ala Thr Gly Leu Thr Asp Ala Ile Lys Asn
            595                 600                 605

Gly Val Glu Gly Ser Ile Asn Asp Phe Thr Ser Pro Gly Glu Thr
    610                 615                 620

Ile Asn Tyr Val Thr Ser His Asp Asn Tyr Thr Leu Trp Asp Lys Ile
625                 630                 635                 640

Ala Leu Ser Asn Pro Asn Asp Ser Glu Ala Asp Arg Ile Lys Met Asp
                645                 650                 655

Glu Leu Ala Gln Ala Val Val Met Thr Ser Gln Gly Val Pro Phe Met
            660                 665                 670

Gln Gly Gly Glu Glu Met Leu Arg Thr Lys Gly Gly Asn Asp Asn Ser
            675                 680                 685

Tyr Asn Ala Gly Asp Ala Val Asn Glu Phe Asp Trp Ser Arg Lys Ala
            690                 695                 700

Gln Tyr Pro Asp Val Phe Asn Tyr Tyr Ser Gly Leu Ile His Leu Arg
705                 710                 715                 720

Leu Asp His Pro Ala Phe Arg Met Thr Thr Ala Asn Glu Ile Asn Ser
                725                 730                 735
```

| His | Leu | Gln | Phe | Leu | Asn | Ser | Pro | Glu | Asn | Thr | Val | Ala | Tyr | Glu | Leu |
|||| 740 |||||| 745 |||||| 750 ||

| Thr | Asp | His | Val | Asn | Lys | Asp | Lys | Trp | Gly | Asn | Ile | Ile | Val | Val | Tyr |
||| 755 |||||| 760 |||||| 765 |||

| Asn | Pro | Asn | Lys | Thr | Val | Ala | Thr | Ile | Asn | Leu | Pro | Ser | Gly | Lys | Trp |
|| 770 |||||| 775 |||||| 780 ||||

| Ala | Ile | Asn | Ala | Thr | Ser | Gly | Lys | Val | Gly | Glu | Ser | Thr | Leu | Gly | Gln |
| 785 |||||| 790 |||||| 795 |||||| 800 |

| Ala | Glu | Gly | Ser | Val | Gln | Val | Pro | Gly | Ile | Ser | Met | Met | Ile | Leu | His |
||||| 805 |||||| 810 |||||| 815 ||

| Gln | Glu | Val | Ser | Pro | Asp | His | Gly | Lys | Lys |
|||| 820 |||||| 825 |

<210> SEQ ID NO 10
<211> LENGTH: 1590
<212> TYPE: DNA
<213> ORGANISM: Artificial Sequence
<220> FEATURE:
<223> OTHER INFORMATION: sequence confirmation after AprE deletion

<400> SEQUENCE: 10

```
tttttcatt ctatcccttt tctgtaaagt ttattttca gaatactttt atcatcatgc     60
tttgaaaaaa tatcacgata atatccattg ttctcacgga agcacacgca ggtcatttga    120
acgaattttt tcgacaggaa tttgccggga ctcaggagca tttaacctaa aaaagcatga    180
catttcagca taatgaacat ttactcatgt ctattttcgt tcttttctgt atgaaaatag    240
ttatttcgag tctctacgga aatagcgaga gatgatatac ctaaatagag ataaaatcat    300
ctcaaaaaaa tgggtctact aaaatattat tccatctatt acaataaatt cacagaatag    360
tcttttaagt aagtctactc tgaattttt taaaaggaga gggtaaagag tgagaagcaa    420
aaaattgtgg atcagcttgt tgtttgcgtt aacgttaatc tttacgatgg cgttcagcaa    480
catgtctgcg caggctgccg gaaaaagcag tacagaaaag aaatacattg tcggatttaa    540
acagacaatg agtgccatga gttccgccaa gaaaaaggat gttatttctg aaaaaggcgg    600
aaaggttcaa aagcaattta agtatgttaa cgcggccgca gcaacattgg atgaaaaagc    660
tgtaaaagaa ttgaaaaaag atccgagcgt tgcatatgtg gaagaagatc atattgcaca    720
tgaatatgcg caatctgttc ctactattgc agtaggtgcg gtaaacagca gcaaccaaag    780
agcttcattc tccagcgcag gttctgagct tgatgtgatg gctcctggcg tgtccatcca    840
aagcacactt cctggaggca cttacggcgc ttataacgga acgtccatgg cgactcctca    900
cgttgccgga gcagcagcgt taattctttc taagcacccg acttggacaa acgcgcaagt    960
ccgtgatcgt ttagaaagca ctgcaacata tcttggaaac tctttctact atggaaaagg   1020
gttaatcaac gtacaagcag ctgcacaata atagtaaaaa gaagcaggtt cctccatacc   1080
tgcttctttt tatttgtcag catcctgatg ttccggcgca ttctcttctt tctccgcatg   1140
ttgaatccgt tccatgatcg acggatggct gcctctgaaa atcttcacaa gcaccggagg   1200
atcaacctgg ctcagccccg tcacggccaa atcctgaaac gttttaacag cggcttctct   1260
gttctctgtc aactcgatcc catactggtc agccttattc tcctgataac gcgagacagc   1320
attagaaaaa ggcgtaaccg caaagctcaa aacagaaaac aaaagcaata acagcggaag   1380
tgccgcaaga tcatgccgcc cttctaaatg aaacatgctg cgggttaggc gaaccgtccg   1440
cttgtaaagc ttatcaatga cataaaatcc ggcgagcgac acgagcaaat agccagccag   1500
```

```
accgatgtaa acgtgcttca tgacataatg gcccatttcg tggcccataa taaacagaat    1560
ttctgaatcg tcaagtttgt tcagcgtcgt                                     1590
```

<210> SEQ ID NO 11
<211> LENGTH: 1705
<212> TYPE: DNA
<213> ORGANISM: Artificial Sequence
<220> FEATURE:
<223> OTHER INFORMATION: sequence confirmation after spoIIAC deletion

<400> SEQUENCE: 11

```
gctcggggct tggcgttatt ttaggaagat acaagcaaat taagcaaatt ggcggagaaa      60
tggttgtttg cgctatctct cctgcggtga agcgattgtt tgatatgtcg ggtctgttta     120
aaattatccg atttgaacaa tctgaacagc aggcactcct gacactgggg gtggcatcat     180
gaaaaatgaa atgcaccttg agttttctgc cctcagtcag aatgaatcgt tcgcccgtgt     240
gacagttgct tcatttatag ctcagctgga cccgacaatg gatgaactga ctgaaatcaa     300
aacagtcgtg tcagaggctg tcacgaatgc gattatccat ggatatgaag agaactgtga     360
agggaaagtt tacatttcag tgacgctgga agatcatgtc gtatatatga ctattcgtga     420
tgaaggctta ggcattacag atcttgaaga agcccgtcag cctctatttta cgactaagcc     480 tgagcttgag cgctctggaa tgggctttac cattatggaa aatttcatgg atgatgtcag     540
tatcgattca tcgcctgaaa tgggaacaac gattcgctta acaaagcact tatcaaaaag     600
caaagcgctt tgtaattaag gagatttgtt atggatgtgg aggttaagaa aaacggcaaa     660
aacgctcagc tgaaggatca tgaagtaaag gaattaatca aacaaagcca aaatggcgac     720
cagcaggcaa gagacctcct catagaaaaa aacatgcgtc ttgtttggtc tgtcgtacag     780 cggttttaa acagaggata tgagcctgac gatctcttcc agatcggctg catcgggcga     840
agaaaaatgg tttgacaaaa ttgcgctgaa agaagcgatc agcgatttgg aggaaaggga     900
aaaactaatc gtctatctca gatattataa agaccagaca cagtccgagg tggctgagcg     960
gctcgggatc tctcaggtgc aggtttccag gcttgaaaag aaaatattaa aacagatcaa    1020
ggttcaaatg gatcatacgg atggctagtc tgcagtgcag gctagctttt ttgtgcaaaa    1080
gcgtggtaat ttatggtctt ttcgagcgga tgaatgagaa caaaatcgaa ccacatacta    1140
catatataac caccgaaaga tggtgatcaa tgatggaacg acgaatattt atccggcttc    1200
gccaccgagt gctggcacat ccaggggata ttattaccgt tggagatgcc gcgcaaatag    1260
aagggcagct tcagctgaaa agaaactttt cggctatgcc gctttatcag gtgagcgaaa    1320
aagataaaaa tatcgtaatt ctggatatca tacaagtcct cagagccatt catttacaag    1380
acccgacaat tgatgttcaa accgtaggcg gagcagaaac cattgttgaa attcagtatc    1440
gaaagcgaaa tttatcaacg gttctatttta tcggtgtctg gctgcttctg tttattggat    1500
cgtgtcttgc catcatgaac tttcatgagg atgtaagcat gagagatgtt catatcgcac    1560
tatatgaaat cataaccgga gagaggaatg actatccata tttgcttcaa atcccataca    1620
gcatcggttt gggactgggg atgatcgtgt tttttaacca catatttaaa aagcgcctaa    1680
atgaagagcc cagcccgctg gaggt                                         1705
```

<210> SEQ ID NO 12
<211> LENGTH: 1596
<212> TYPE: DNA
<213> ORGANISM: Artificial Sequence
<220> FEATURE:
<223> OTHER INFORMATION: sequence confirmation after NprE deletion

<400> SEQUENCE: 12

```
ttgtctgctt aatataaaat aacgttcgaa atgcaataca taatgactga ataactccaa    60
cacgaacaac aatcctttac ttcttattaa ggcctcattc ggttagacag cggacttttc   120
aaaaagtttc aagatgaaac aaaaatatct catcttcccc ttgatatgta aaaacataa    180
ctcttgaatg aaccaccaca tgacacttga ctcatcttga tattattcaa caaaaacaaa   240
cacaggacaa tactatcaat tttgtctagt tatgttagtt tttgttgagt attccagaat   300
gctagtttaa tataacaata taaagttttc agtattttca aaaggggga tttattgtgg    360
gtttaggtaa gaaattgtct gttgctgtcg ctgcttcgtt tatgagttta tcaatcagcc   420
tgccaggtgt tcaggctgct gaaggtcatc agcttaaaga gaatcaaaca aatttcctct   480
ccaaaaacgc gattgcgcaa tcagaactct ctgcaccaaa tgacaaggct gtcaagcagt   540
ttttgaaaaa gaacagcaac attttaaag gtgacccttc caaaaggctg aagcttgttg    600
aaagcacgac tgatgccctt ggatacaagc actttcgata tgcgcctgtc gttaacggag   660
tgccaattaa agattcgcaa gtgatcgttc acgtcgataa atccgataat gtctatgcgg   720
tcaatggtga attacacaat caatctgctg caaaaacaga taacagccaa aaagtctctt   780
ctgaaaaagc gctggcactc gctttcaaag ctatcggcaa atcaccagac gctgtttcta   840
acggagcggc caaaaacagc aataaagccg aattaaaagc gtaacgatac agaagactgg   900
gacatcggtg aagacattac ggtcagccag cctgctcttc gcagcctgtc caaccctaca   960
aaatacaacc agcctgacaa ttacgccaat taccgaaacc ttccaaacac agatgaaggc  1020
gattatggcg gtgtacacac aaacagcgga attccaaaca aagccgctta caacaccatc  1080
acaaaacttg gtgtatctaa atcacagcaa atctattacc gtgcgttaac aacgtacctc  1140
acgccttctt ccacgttcaa agatgccaag gcagctctca ttcagtctgc ccgtgacctc  1200
tacggctcaa ctgatgccgc taaagttgaa gcagcctgga atgctgttgg attgtaatat  1260
taggaaaagc ctgagatccc tcaggctttt attgttacat atcttgattt ctctctcagc  1320
tgaaacgacg aaaagatgct gccatgagac agaaaaccgc tcctgatttg cataaagagg  1380
gatgcagccg caagtgcgca ttttataaaa gctaatgatt cagtccacat aattgataga  1440
cgaattctgc tacaggtcac gtggctatgt gaaggatcgc gcgtccagtt aagagcaaaa  1500
acattgacaa aaaatttat ttatgctaaa atttactatt aatatatttg tatgtataat   1560
aagattctcc tggccagggg aatcttattt tttgtg                             1596
```

<210> SEQ ID NO 13
<211> LENGTH: 44
<212> TYPE: DNA
<213> ORGANISM: Artificial Sequence
<220> FEATURE:
<223> OTHER INFORMATION: pksb-apr_czF1 primer sequence

<400> SEQUENCE: 13

```
ggtatcgata agcttcctgc agatctctca ggagcattta acct              44
```

<210> SEQ ID NO 14
<211> LENGTH: 35
<212> TYPE: DNA
<213> ORGANISM: Artificial Sequence
<220> FEATURE:
<223> OTHER INFORMATION: pksb-apr_R1 primer sequence

<400> SEQUENCE: 14

```
gcacctactg caatagtaag gaacagattg cgcat                  35
```

<210> SEQ ID NO 15
<211> LENGTH: 35
<212> TYPE: DNA
<213> ORGANISM: Artificial Sequence
<220> FEATURE:
<223> OTHER INFORMATION: pksb-apr_F2 primer sequence

<400> SEQUENCE: 15
atgcgcaatc tgttccttac tattgcagta ggtgc                          35

<210> SEQ ID NO 16
<211> LENGTH: 44
<212> TYPE: DNA
<213> ORGANISM: Artificial Sequence
<220> FEATURE:
<223> OTHER INFORMATION: pksb-apr_czR2 primer sequence

<400> SEQUENCE: 16
aatatggcgg ccgcgaattc agatctctaa tgctgtctcg cgtt                44

<210> SEQ ID NO 17
<211> LENGTH: 41
<212> TYPE: DNA
<213> ORGANISM: Artificial Sequence
<220> FEATURE:
<223> OTHER INFORMATION: pksb-npr_czF1 primer sequence

<400> SEQUENCE: 17
ggtatcgata agcttcctgc agatctcatc ttccccttga t                   41

<210> SEQ ID NO 18
<211> LENGTH: 34
<212> TYPE: DNA
<213> ORGANISM: Artificial Sequence
<220> FEATURE:
<223> OTHER INFORMATION: pksb-npr_R1 primer sequence

<400> SEQUENCE: 18
cagtcttctg tatcgttacg cttttaattc ggct                           34

<210> SEQ ID NO 19
<211> LENGTH: 34
<212> TYPE: DNA
<213> ORGANISM: Artificial Sequence
<220> FEATURE:
<223> OTHER INFORMATION: pksb-npr_F2 primer sequence

<400> SEQUENCE: 19
agccgaatta aaagcgtaac gatacagaag actg                           34

<210> SEQ ID NO 20
<211> LENGTH: 41
<212> TYPE: DNA
<213> ORGANISM: Artificial Sequence
<220> FEATURE:
<223> OTHER INFORMATION: pksb-npr_czR2 primer sequence

<400> SEQUENCE: 20
tatggcggcc gcgaattcag atctcctggc caggagaatc t                   41

<210> SEQ ID NO 21
<211> LENGTH: 46
<212> TYPE: DNA
<213> ORGANISM: Artificial Sequence
<220> FEATURE:
<223> OTHER INFORMATION: pksb-spo_czF1 primer sequence

<400> SEQUENCE: 21
ggtatcgata agcttcctgc aggaacaatc tgaacagcag gcactc                46

<210> SEQ ID NO 22
<211> LENGTH: 39
<212> TYPE: DNA
<213> ORGANISM: Artificial Sequence
<220> FEATURE:
<223> OTHER INFORMATION: pksb-spo_R1 primer sequence

<400> SEQUENCE: 22
ttgtcaaacc atttttcttc gcccgatgca gccgatctg                        39

<210> SEQ ID NO 23
<211> LENGTH: 39
<212> TYPE: DNA
<213> ORGANISM: Artificial Sequence
<220> FEATURE:
<223> OTHER INFORMATION: pksb-spo_F2 primer sequence

<400> SEQUENCE: 23
cagatcggct gcatcgggcg aagaaaaatg gtttgacaa                        39

<210> SEQ ID NO 24
<211> LENGTH: 44
<212> TYPE: DNA
<213> ORGANISM: Artificial Sequence
<220> FEATURE:
<223> OTHER INFORMATION: pksb-spo_czR2 primer sequence

<400> SEQUENCE: 24
atatggcggc cgcgaattca gatctgttca tgatggcaag acac                  44

<210> SEQ ID NO 25
<211> LENGTH: 956
<212> TYPE: PRT
<213> ORGANISM: Bacillus deramificans
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (619)..(619)
<223> OTHER INFORMATION: Xaa can be any naturally occurring amino acid
<220> FEATURE:
<221> NAME/KEY: misc_feature
<222> LOCATION: (811)..(811)
<223> OTHER INFORMATION: Xaa can be any naturally occurring amino acid

<400> SEQUENCE: 25

Met Ala Lys Lys Leu Ile Tyr Val Cys Leu Ser Val Cys Leu Val Leu
 1               5                  10                  15

Thr Trp Ala Phe Asn Val Lys Gly Gln Ser Ala His Ala Asp Gly Asn
             20                  25                  30

Thr Thr Thr Ile Ile Val His Tyr Phe Cys Pro Ala Gly Asp Tyr Gln
         35                  40                  45

Pro Trp Ser Leu Trp Met Trp Pro Lys Asp Gly Gly Ala Glu Tyr
     50                  55                  60

Asp Phe Asn Gln Pro Ala Asp Ser Phe Gly Ala Val Ala Ser Ala Asp
65                  70                  75                  80

Ile Pro Gly Asn Pro Ser Gln Val Gly Ile Ile Val Arg Thr Gln Asp
                 85                  90                  95

```
Trp Thr Lys Asp Val Ser Ala Asp Arg Tyr Ile Asp Leu Ser Lys Gly
            100                 105                 110

Asn Glu Val Trp Leu Val Glu Gly Asn Ser Gln Ile Phe Tyr Asn Glu
        115                 120                 125

Lys Asp Ala Glu Asp Ala Ala Lys Pro Ala Val Ser Asn Ala Tyr Leu
    130                 135                 140

Asp Ala Ser Asn Gln Val Leu Val Lys Leu Ser Gln Pro Leu Thr Leu
145                 150                 155                 160

Gly Glu Gly Xaa Ser Gly Phe Thr Val His Asp Thr Ala Asn Lys
                165                 170                 175

Asp Ile Pro Val Thr Ser Val Lys Asp Ala Ser Leu Gly Gln Asp Val
            180                 185                 190

Thr Ala Val Leu Ala Gly Thr Phe Gln His Ile Phe Gly Gly Ser Asp
        195                 200                 205

Trp Ala Pro Asp Asn His Ser Thr Leu Leu Lys Lys Val Thr Asn Asn
    210                 215                 220

Leu Tyr Gln Phe Ser Gly Asp Leu Pro Glu Gly Asn Tyr Gln Tyr Lys
225                 230                 235                 240

Val Ala Leu Asn Asp Ser Trp Asn Asn Ser Tyr Pro Ser Asp Asn Ile
            245                 250                 255

Asn Leu Thr Val Pro Ala Gly Gly Ala His Val Thr Phe Ser Tyr Ile
        260                 265                 270

Pro Ser Thr His Ala Val Tyr Asp Thr Ile Asn Asn Pro Asn Ala Asp
    275                 280                 285

Leu Gln Val Glu Ser Gly Val Lys Thr Asp Leu Val Thr Val Thr Leu
290                 295                 300

Gly Glu Asp Pro Asp Val Ser His Thr Leu Ser Ile Gln Thr Asp Gly
305                 310                 315                 320

Tyr Gln Ala Lys Gln Val Ile Pro Arg Asn Val Leu Asn Ser Ser Gln
            325                 330                 335

Tyr Tyr Tyr Ser Gly Asp Asp Leu Gly Asn Thr Tyr Thr Gln Lys Ala
        340                 345                 350

Thr Thr Phe Lys Val Trp Ala Pro Thr Ser Thr Gln Val Asn Val Leu
    355                 360                 365

Leu Tyr Asp Ser Ala Thr Gly Ser Val Thr Lys Ile Val Pro Met Thr
370                 375                 380

Ala Ser Gly His Gly Val Trp Glu Ala Thr Val Asn Gln Asn Leu Glu
385                 390                 395                 400

Asn Trp Tyr Tyr Met Tyr Glu Val Thr Gly Gln Gly Ser Thr Arg Thr
            405                 410                 415

Ala Val Asp Pro Tyr Ala Thr Ala Ile Ala Pro Asn Gly Thr Arg Gly
        420                 425                 430

Met Ile Val Asp Leu Ala Lys Thr Asp Pro Ala Gly Trp Asn Ser Asp
    435                 440                 445

Lys His Ile Thr Pro Lys Asn Ile Glu Asp Glu Val Ile Tyr Glu Met
450                 455                 460

Asp Val Arg Asp Phe Ser Ile Asp Pro Asn Ser Gly Met Lys Asn Lys
465                 470                 475                 480

Gly Lys Tyr Leu Ala Leu Thr Glu Lys Gly Thr Lys Gly Pro Asp Asn
            485                 490                 495

Val Lys Thr Gly Ile Asp Ser Leu Lys Gln Leu Gly Ile Thr His Val
        500                 505                 510
```

```
Gln Leu Met Pro Val Phe Ala Ser Asn Ser Val Asp Glu Thr Asp Pro
            515                 520                 525

Thr Gln Asp Asn Trp Gly Tyr Asp Pro Arg Asn Tyr Asp Val Pro Glu
        530                 535                 540

Gly Gln Tyr Ala Thr Asn Ala Asn Gly Asn Ala Arg Ile Lys Glu Phe
545                 550                 555                 560

Lys Glu Met Val Leu Ser Leu His Arg Glu His Ile Gly Val Asn Met
            565                 570                 575

Asp Val Val Tyr Asn His Thr Phe Ala Thr Gln Ile Ser Asp Phe Asp
        580                 585                 590

Lys Ile Val Pro Glu Tyr Tyr Arg Thr Met Ile Gln Val Ile Ile
            595                 600                 605

Pro Thr Asp Gln Val Leu Glu Met Lys Leu Xaa Ala Glu Arg Pro Met
        610                 615                 620

Val Gln Lys Phe Ile Ile Asp Ser Leu Lys Tyr Trp Val Asn Glu Tyr
625                 630                 635                 640

His Ile Asp Gly Phe Arg Phe Asp Leu Met Ala Leu Leu Gly Lys Asp
            645                 650                 655

Thr Met Ser Lys Ala Ala Ser Glu Leu His Ala Ile Asn Pro Gly Ile
        660                 665                 670

Ala Leu Tyr Gly Glu Pro Trp Thr Gly Gly Thr Ser Ala Leu Pro Asp
            675                 680                 685

Asp Gln Leu Leu Thr Lys Gly Ala Gln Lys Gly Met Gly Val Ala Val
        690                 695                 700

Phe Asn Asp Asn Leu Arg Asn Ala Leu Asp Gly Asn Val Phe Asp Ser
705                 710                 715                 720

Ser Ala Gln Gly Phe Ala Thr Gly Ala Thr Gly Leu Thr Asp Ala Ile
            725                 730                 735

Lys Asn Gly Val Glu Gly Ser Ile Asn Asp Phe Thr Ser Ser Pro Gly
        740                 745                 750

Glu Thr Ile Asn Tyr Val Thr Ser His Asp Asn Tyr Thr Leu Trp Asp
            755                 760                 765

Lys Ile Ala Leu Ser Asn Pro Asn Asp Ser Glu Ala Asp Arg Ile Lys
        770                 775                 780

Met Asp Glu Leu Ala Gln Ala Val Val Met Thr Ser Gln Gly Val Pro
785                 790                 795                 800

Phe Met Gln Gly Gly Glu Glu Met Leu Arg Xaa Lys Gly Gly Asn Asp
            805                 810                 815

Asn Ser Tyr Asn Ala Gly Asp Ala Val Asn Glu Phe Asp Trp Ser Arg
        820                 825                 830

Lys Ala Gln Tyr Pro Asp Val Phe Asn Tyr Tyr Ser Gly Leu Ile His
            835                 840                 845

Leu Arg Leu Asp His Pro Ala Phe Arg Met Thr Thr Ala Asn Glu Ile
        850                 855                 860

Asn Ser His Leu Gln Phe Leu Asn Ser Pro Glu Asn Thr Val Ala Tyr
865                 870                 875                 880

Glu Leu Thr Asp His Val Asn Lys Asp Lys Trp Gly Asn Ile Ile Val
            885                 890                 895

Val Tyr Asn Pro Asn Lys Thr Val Ala Thr Ile Asn Leu Pro Ser Gly
        900                 905                 910

Lys Trp Ala Ile Asn Ala Thr Ser Gly Lys Val Gly Glu Ser Thr Leu
            915                 920                 925
```

-continued

```
Gly Gln Ala Glu Gly Ser Val Gln Val Pro Gly Ile Ser Met Met Ile
        930             935             940

Leu His Gln Glu Val Ser Pro Asp His Gly Lys Lys
945             950             955
```